United States Patent [19]

Ratcliffe

[11] Patent Number: 5,576,305
[45] Date of Patent: Nov. 19, 1996

[54] INTERCELLULAR ADHESION MEDIATORS

[75] Inventor: Robert M. Ratcliffe, Carlsbad, Calif.

[73] Assignee: Cytel Corporation, San Diego, Calif.

[21] Appl. No.: 466,040

[22] Filed: Jun. 6, 1995

Related U.S. Application Data

[63] Continuation-in-part of Ser. No. 63,181, May 14, 1993, which is a continuation-in-part of Ser. No. 810,789, Dec. 17, 1991, abandoned, which is a continuation-in-part of Ser. No. 716,735, Jun. 17, 1991, abandoned, which is a continuation-in-part of Ser. No. 632,390, Dec. 21, 1990, abandoned, which is a continuation-in-part of Ser. No. 619,319, Nov. 28, 1990, abandoned, which is a continuation-in-part of Ser. No. 538,853, Jun. 15, 1990, abandoned.

[51] Int. Cl.$^6$ .............................. A61K 31/73; C07H 3/06
[52] U.S. Cl. ............................... 514/25; 514/54; 514/62; 536/17.2; 536/53; 536/55.2
[58] Field of Search ............................ 514/25, 54, 62; 536/17.2, 53, 55.2

[56] References Cited

U.S. PATENT DOCUMENTS

| | | | |
|---|---|---|---|
| 5,211,936 | 5/1993 | Brandley et al. | 424/1.73 |
| 5,211,937 | 5/1993 | Brandley et al. | 424/1.73 |
| 5,378,464 | 1/1995 | McEver | 424/143.1 |

FOREIGN PATENT DOCUMENTS

| | | |
|---|---|---|
| WO90/13300 | 11/1990 | WIPO . |
| WO91/19502 | 12/1991 | WIPO . |
| WO92/07572 | 5/1992 | WIPO . |

OTHER PUBLICATIONS

Johnson, Philip H., et al. (1985) "Sialyl compounds as acceptor substrates for the human α–3– and α–3/4–L–fucosyltransferases", *Biochem. Soc. Trans.*, 13(6):1119–1120.

Ching, C. K., et al. (1990) "Purification and Characterization of a Peanut–Agglutination–Binding Pancreatic–Cancer–Related Serum Mucus Glycoprotein", *Int. J. Cancer*, 45:1022–1027.

Rosen, Steven D., et al. (1986) "Lymphocyte attachment to high endothelial venules during recirculation: A possible role for carbohydrates as recognition determinants", *Molecular and Cellular Biochemistry*, 72:153–164.

Underhill, Charles, et al. (1978) "The Role of Hyaluronic Acid in Intercellular Adhesion of Cultured Mouse Cells", *Experimental Cell Research*, 117:155–164).

Picker, Louis J., et al. (1991) "The Neutrophil Selectin LECAM–1 Present Carbohydrate Ligands to the Vascular Selectins ELAM–1 and GMP–140", *Cell* 66:921–933.

Tyrrell, David, et al. (1991) "Structural requirements for the carbohydrate ligand of E–selectin", *Proc. Natl. Acad. Sci. USA*, 88:10372–10376.

Lowe, John B., et al. (1990) "ELAM–1–Dependent Cell Adhesion to Vascular Endothelium Determined by a Transfected Human Fucosyltransferase cDNA", *Cell*, 63:475–484.

Derwent Publications Ltd., London, GB; AN 90–135674 & JP–A–02 83 337 (Nichirei KK) Mar. 23, 1990, Abstract.

Kannagi, Reiji, et al. (1982) "Possible role of ceramide in defining structural and function of membrane glycolipids", *Proc. Natl. Acad. Sci USA*, 79:3470–3474.

Hakomori, Sen–itiroh, et al. (1984) "Novel Fucolipids Accumulating in Human Adenocarcinoma", *The Journal of Biological Chemistry*, 259(7):4672–4680.

Fukushi, Yasuo, et al. (1984) "Novel Fucolipids Accumulating in Human Adenocacinoma", *The Journal of Biological Chemistry*, 259(16):10511–10517.

Holmes, Eric H., et al. (1985) "Enzymatic Basis for the Accumulation of Glycolipids with X and Dimeric X Determinants in Human Lung Cancer Cells" (NCI–H69), *The Journal of Biological Chemistry*, 260(12):7619–7627.

Fukuda, Michiko N., et al. (1986) "Structure of a Novel Pialylated Fucosyl Lacto–N–nor–hexaosylceramide Isolated from Chronic Myelogenous Leukemia Cells", *The Journal Of Biological Chemistry*, 261(50:2376–2383.

McIntire, Floyd C., et al. (1988) "A Polysaccharide from Streptococcus sanguis 34 that inhibits Coaggregation of S. sanguis 34 with Actinomyces viscosus T14V", *Journal of Bacteriology*, 170(5):2229–2235.

Nilsson, Kurt G. I. (1988) "Enzymatic synthesis of oligosaccharidddes" *Trnes in Biotechnology*, 6:256–264.

Cassels, Frederick J., et al. (1989) "Isolation of a Coaggregation–Inhibiting Cell Wall Polysaccharide from Streptococcus sanguis H1", *Journal of Bacteriology*, 171(7):4019–4025.

Finne, Jukka, et al. (1989) "Novel Polyfucosylated N–linked Glycopeptides with Blood Group A,H,X and Y Determinatns from Human Small Intestinal Epithelial Cells", *The Journal of Biological Chemistry*, 264(10):5720–5735.

Levery, Steven B., et al. (1988) "H–N.M.R. Analysis of Type–2 Chain Lacto–Gangliosides. Confirmation of Structure of a Novel Cancer–Associated Fucoganglioside", Carbohydrate Research, 178:121–144.

Hakomori, et al. (1984) *J. Biol Chem.*, 259(7):4672–4680.

Sakura (1989) *Chemical Abstracts*, 111:151639b.

*Primary Examiner*—Gary L. Kunz
*Assistant Examiner*—Kathleen Kahler Fonda
*Attorney, Agent, or Firm*—Townsend and Townsend and Crew LLP

[57] ABSTRACT

The present invention is directed towards compositions and methods for reducing or controlling inflammation and for treating inflammatory disease processes and other pathological conditions mediated by intercellular adhesion. The compositions of the invention include compounds that selectively bind selectin receptors, the selectin binding activity being mediated by a carbohydrate moiety. The selectin-binding moieties of the invention are derivatives of a sialylated, fucosylated N-acetyllactosamine unit of the Lewis X antigen. Compounds containing a selectin-binding moiety in both monovalent and multivalent forms are included in the invention. The compounds of the invention are provided as pharmaceutical compositions which include, for example, liposomes that carry selectin-binding moieties of the invention.

8 Claims, 21 Drawing Sheets

| | | |
|---|---|---|
| XVII | 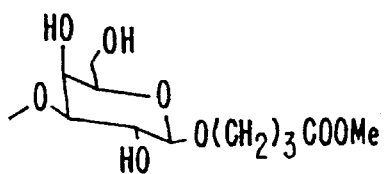 | 1.0 |
| XVIII | 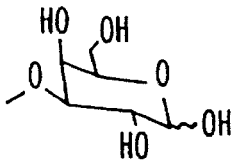 | 1.0 |
| XIX | 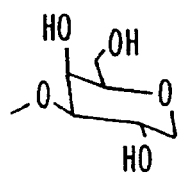 | 1.0 |
| XX | 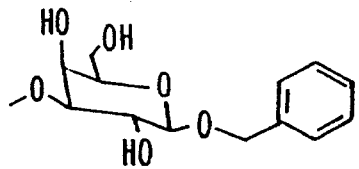 | 1.0 |
| XXIII | 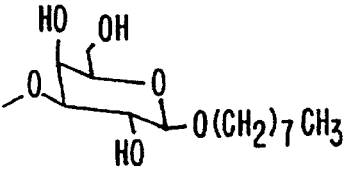 | 2.0 |
| XXIV | 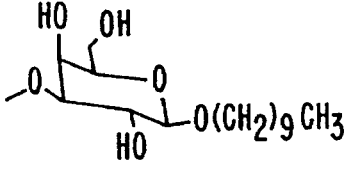 | 2.5 |
| XXV | 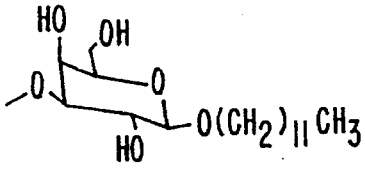 | 3.7 |
| XXVI | 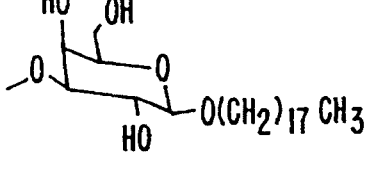 | 3.7 |
FIG. 12B-2.

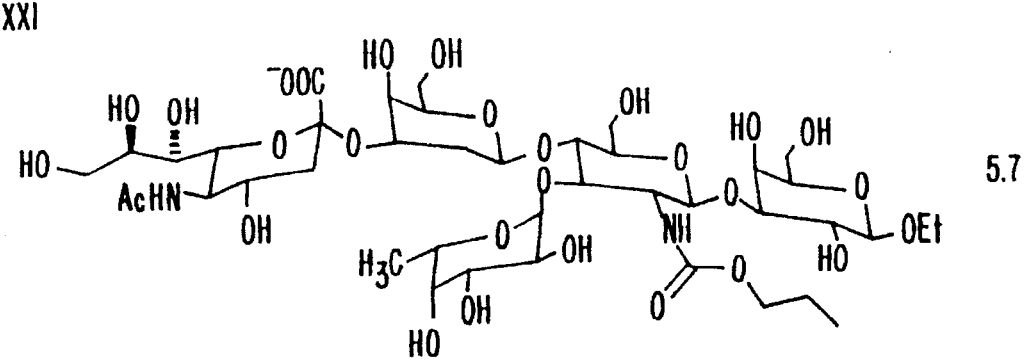
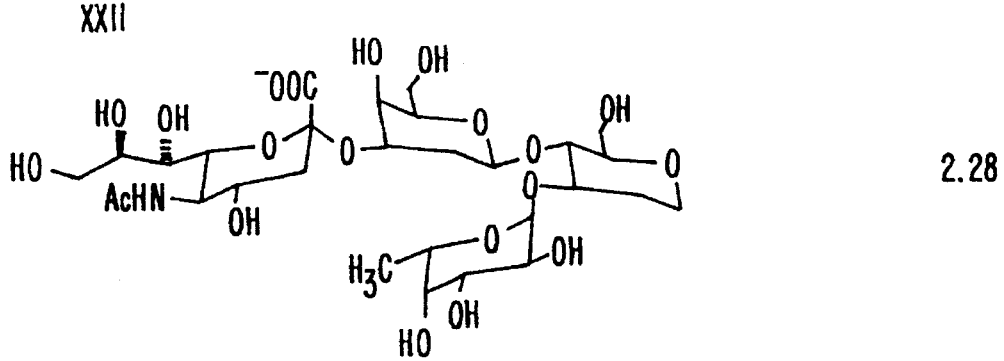
FIG. 12B-3.
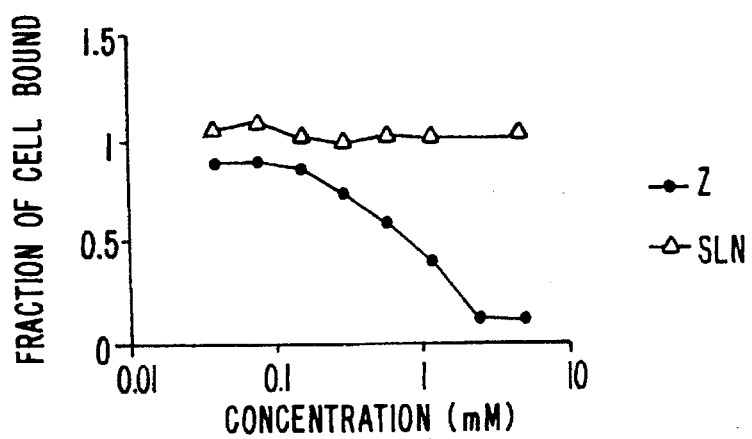
FIG. 13.

PANEL A

PANEL B

PANEL C

PANEL A

PANEL B

PANEL C

FRAME A

FRAME B

FRAME C

PANEL A

PANEL B

PANEL C

FRAME A

FRAME B

FRAME C

PANEL A

PANEL B

PANEL C

FRAME A

FRAME B

INTERCELLULAR ADHESION MEDIATORS

CROSS-REFERENCE TO RELATED APPLICATIONS

This application is a continuation-in-part of U.S. Ser. No. 08/063,181 (filed May 14, 1993) which is a continuation-in-part of U.S. Ser. No. 07/810,789, now abandoned, (filed Dec. 17, 1991) which is a continuation in part of 07/716,735, now abandoned, (filed Jun. 17, 1991), which is a continuation-in-part of U.S. Ser. No. 07/632,390, now abandoned, (filed Dec. 21, 1990), which is a continuation-in-part of U.S. Ser. No. 07/619,319, now abandoned, (filed Nov. 28, 1990), which is a continuation in-part of Ser. No. 07/538,853, now abandoned, (filed Jun. 15, 1990), all of which disclosures are herein incorporated by reference.

FIELD OF THE INVENTION

The present invention relates to compositions and methods for reducing or controlling inflammation and for treating inflammatory disease processes and other pathological conditions mediated by intercellular adhesion.

BACKGROUND OF THE INVENTION

Vascular endothelial cells and blood platelets play key roles in a number of biological responses by selectively binding certain cells, for instance phagocytic leukocytes, in the blood stream. For example, endothelial cells preferentially bind monocytes and granulocytes prior to their migration through the blood vessel wall and into surrounding tissue in an inflammatory response. Certain inflammation-triggering compounds are known to act directly on the vascular endothelium to promote the adhesion of leukocytes to vessel walls. Cells then move through the walls and into areas of injury or infection. Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes which are thought to be mediated by this process include atherosclerosis, blood clotting and inflammation.

Recent work has revealed that specialized cell surface receptors on endothelial cells and platelets, designated endothelial leukocyte adhesion molecule-1 (ELAM-1, E-Selectin) and granule membrane protein-140 (GMP-140, P-Selectin), respectively, are involved in the recognition of various circulating cells by the endothelium and platelets. These receptors are surface glycoproteins with a lectin-like domain, a region with homology to epidermal growth factor, and a region with homology to complement regulatory proteins (see, Bevilacqua et al., Science 243:1160 (1989), which is incorporated herein by reference). For example, E-Selectin has been shown to mediate endothelial leukocyte adhesion, which is the first step in many inflammatory responses. Specifically, E-Selectin binds human neutrophils, monocytes, eosinophils, certain T-lymphocytes (N. Graber et al., J. Immunol., 145:819 (1990)), NK cells, and the promyelocytic cell line HL-60.

The term "selectin" has been suggested for a general class of receptors, which includes E-Selectin and P-Selectin because of their lectin-like domain and the selective nature of their adhesive functions. These cell surface receptors are expressed on a variety of cells. P-Selectin (also known as PADGEM) is present on the surface of platelets and endothelial cells, where it mediates platelet-leukocyte and endothelium-leukocyte interactions. Another member of the selectin class is the MEL-14 antigen, and its human analog LAM-1, which are cell surface receptors of lymphocytes, and act as lymph node homing receptors. The exact nature of the ligand recognized by selectin receptors remains unknown.

Various other methods have been previously developed to block the action of selectins and thus inhibit cellular adhesion. For instance, the use of monoclonal antibodies directed to E-Selectin has been proposed as a method to inhibit endothelial-leukocyte adhesion as a treatment for pathological responses, such as inflammation. Endothelial interleukin-8 has also been shown to be an inhibitor of leukocyte-endothelial interactions.

With the elucidation of the ligand-receptor interaction, it will be possible to develop highly specific, efficient inhibitors of selectin-mediated cellular adhesion which would be useful in therapeutic regimens. The ligand(s) could also be used to target other pharmaceutical compounds, such as anti-inflammatory agents or anti-oxidants, to the sites of injury. To date, insufficient understanding of the interaction of the ligand(s) and receptor molecules on the respective cells has hindered these efforts. The present invention fulfills these and other related needs.

SUMMARY OF THE INVENTION

Novel compositions comprising compounds which selectively bind selectin receptors are provided by the present invention. The compounds of the invention comprise at least one selectin-binding carbohydrate moiety. The selectin-binding moieties are derivatives of a sialylated, fucosylated N-acteyllactosamine unit of the Lewis X antigen In particular, the present invention provides pharmaceutical compositions comprising a pharmaceutically acceptable carrier and a compound having the formula:

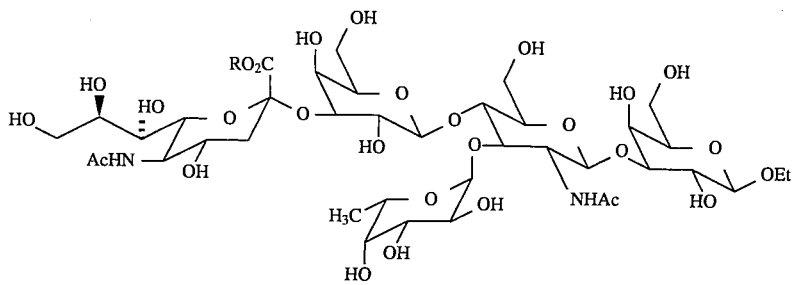

in which R is an alkyl group, preferably methyl, ethyl, propyl, isopropyl, butyl, isobutyl, tert-butyl, pentyl or hexyl.

The present invention further provides intermediates which are useful in the preparation of the pharmaceutical compositions above. In particular, the intermediates are either lactones or esters, having the formulae (IIa), (IIb) and (III), respectively,

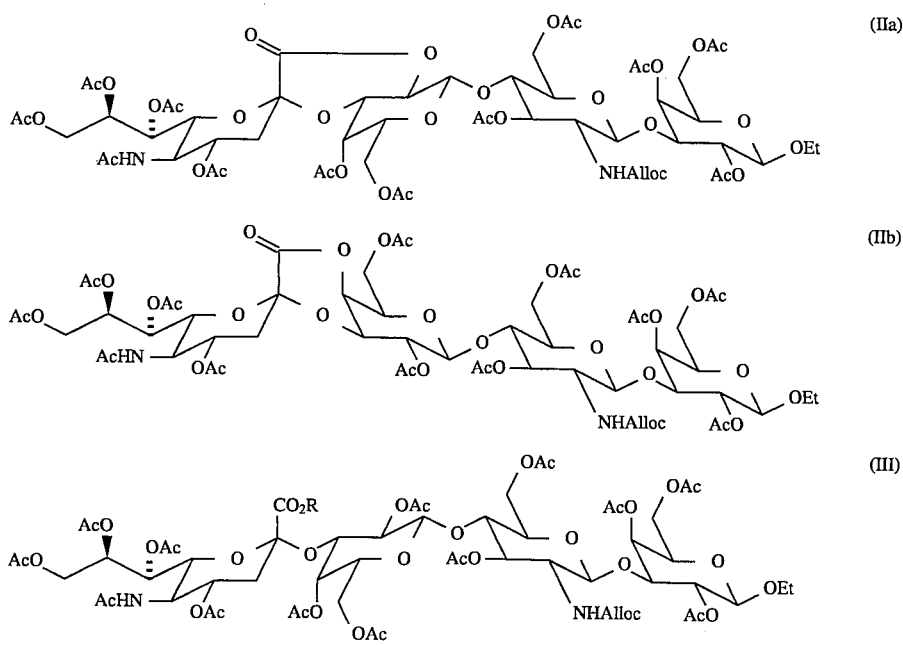

in which R is alkyl, preferably methyl, ethyl, propyl, benzyl, butyl or pentyl.

The invention further provides a process for the preparation of compounds of formula I, comprising:

(a) preparing a lactone intermediate of formula (IIa) or (IIb);

(b) treating the lactone intermediate with an alkoxide to form an ester intermediate of formula (III); and (c) deprotecting and fucosylating the ester intermediate to provide the pharmaceutical agents of formula (I).

The invention further provides a single step process by which compound VIII, below, is converted to compound IX.

The pharmaceutical compositions are useful in methods of inhibiting intercellular adhesion in a patient for a disease process, such as inflammation. The selectin receptor, such as E-Selectin or P-Selectin, may be expressed on vascular endothelial cells or platelets. The inflammatory process may be, for example, septic shock, wound associated sepsis, rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

BRIEF DESCRIPTION OF THE FIGURES

(FIG. 2A) and 4° C. (FIG. 2B) compared to monoclonal antibodies which do not bind $SLe_x$ determinants.

FIG. 13 shows inhibition of binding of HL-60 cells to recombinant E-selectin in a concentration dependent manner by Z but not by the non-fucosylated derivative SLN.

DESCRIPTION OF THE PREFERRED EMBODIMENT

Figure 1:
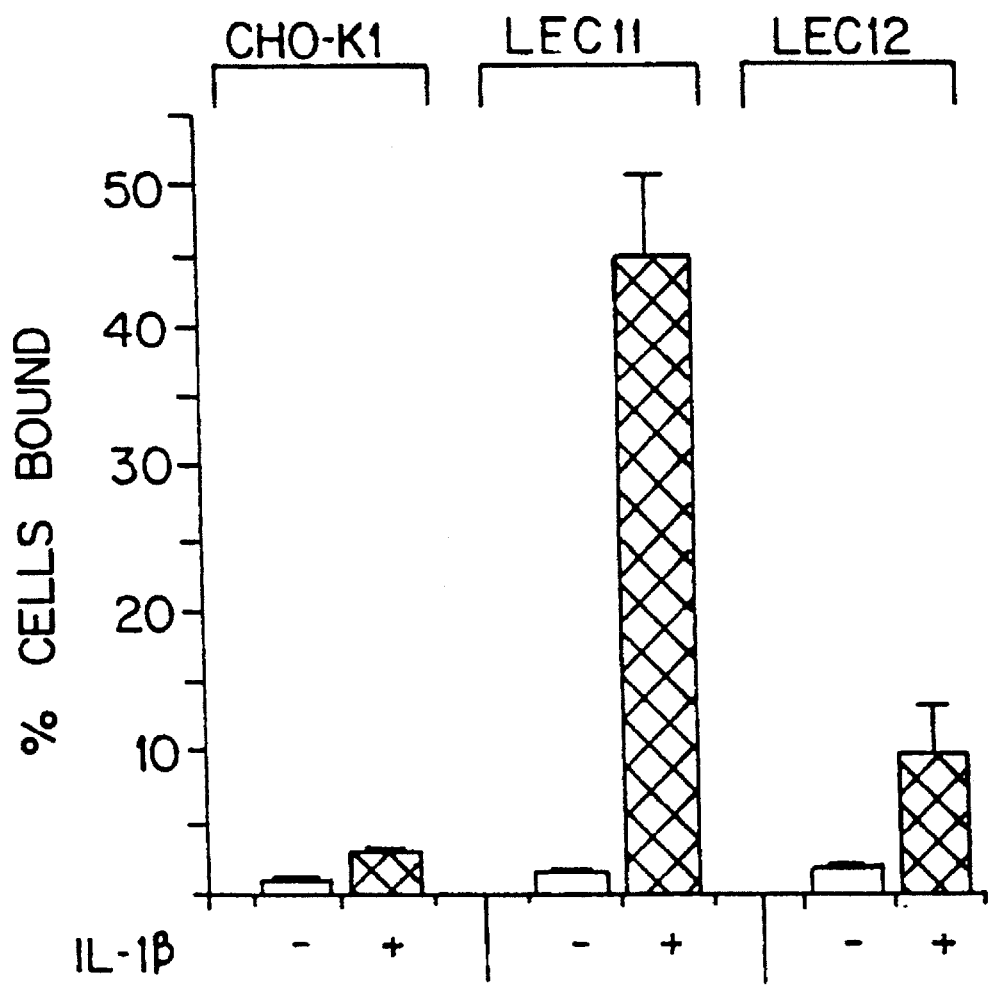
FIG. 1 illustrates the ability of cells which express $SLe^x$ (LEC 11) to bind to IL-1$\beta$ activated endothelial cells compared to those cells which express non-sialylated $Le^x$ (CHO-K1 and LEC 12).
Figure 2A:
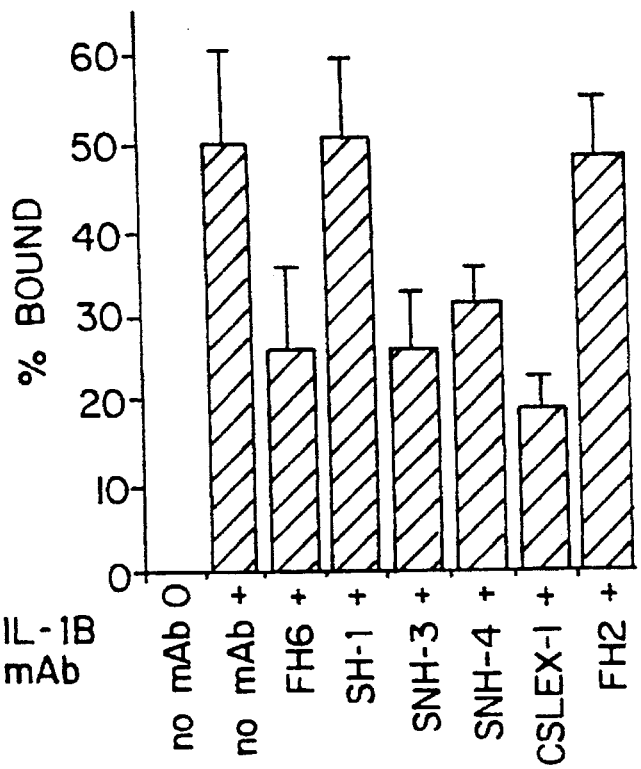
FIGS. 2A and 2B illustrate the ability of monoclonal antibodies specific for $SLe^x$ to block selectin-mediated binding of HL-60 cells at 37° C.
Figure 2B:
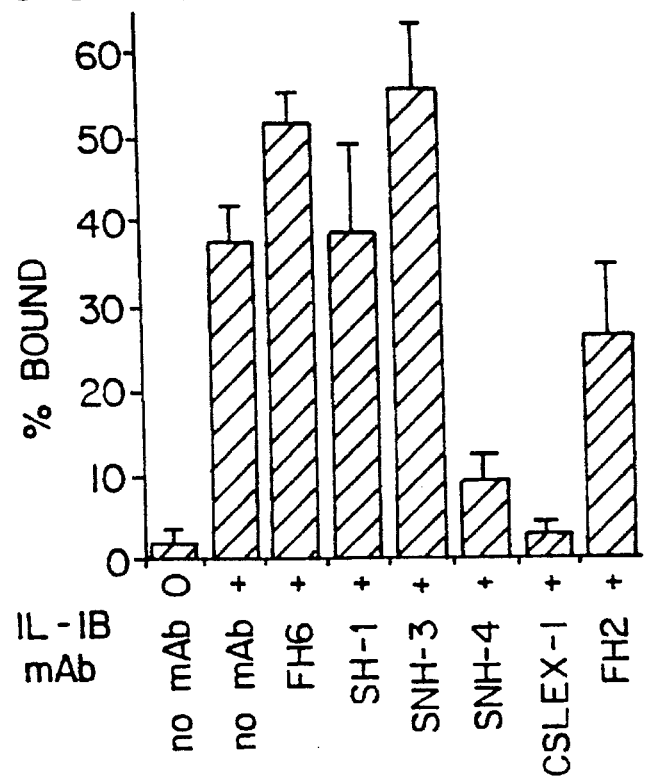
Figure 3A:
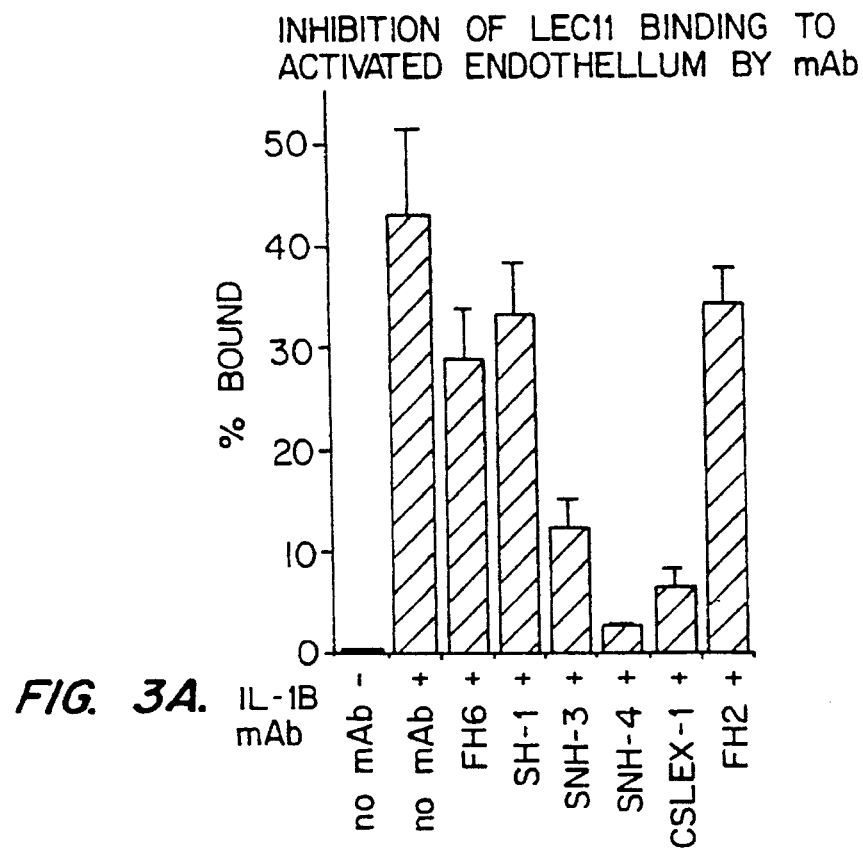
FIGS. 3A and 3B illustrate the effects of incubating LEC 11 (FIG. 3A) and LEC 12 (FIG. 3B) cells with $SLe^x$ and non-$SLe^x$ specific monoclonal antibodies on binding to activated endothelial cells.
Figure 3B:
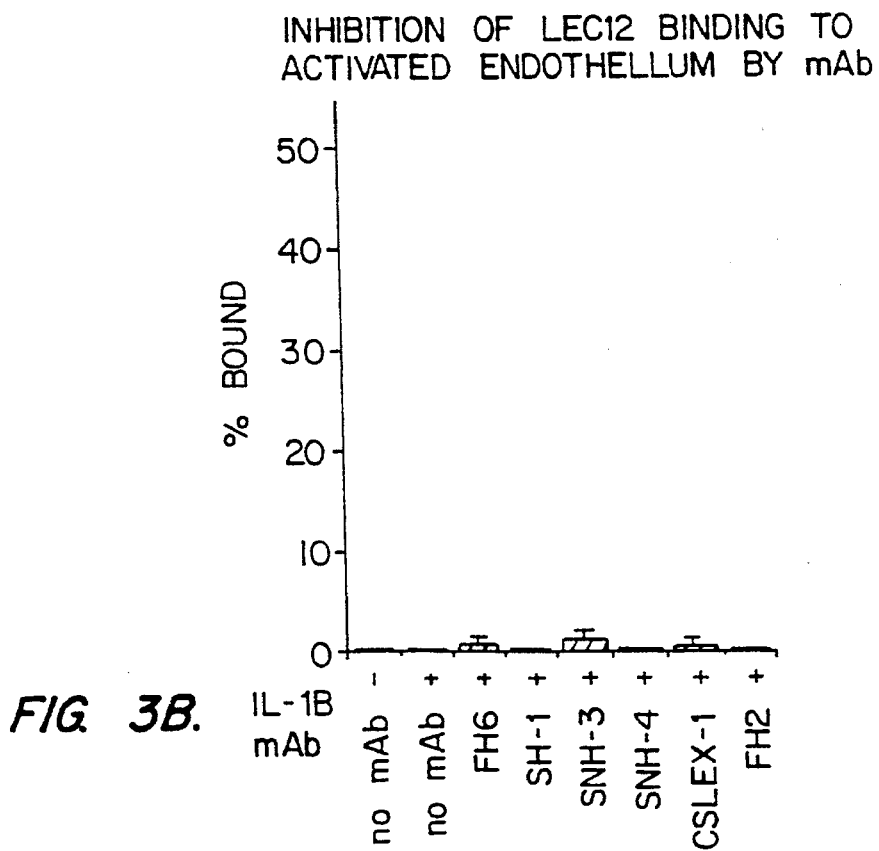
Figure 4:
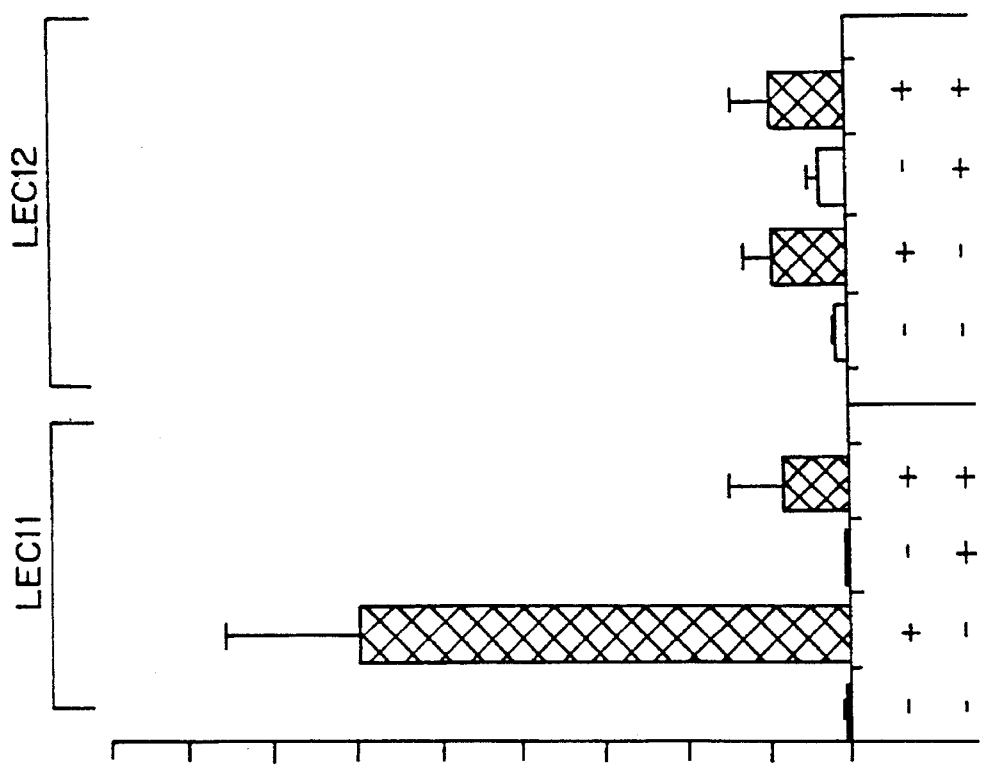
FIGS. 4A and 4B illustrate the results obtained by treating HL-60, LEC11 and LEC12 cells with sialidase before binding to activated endothelial cells.
Figure 4:
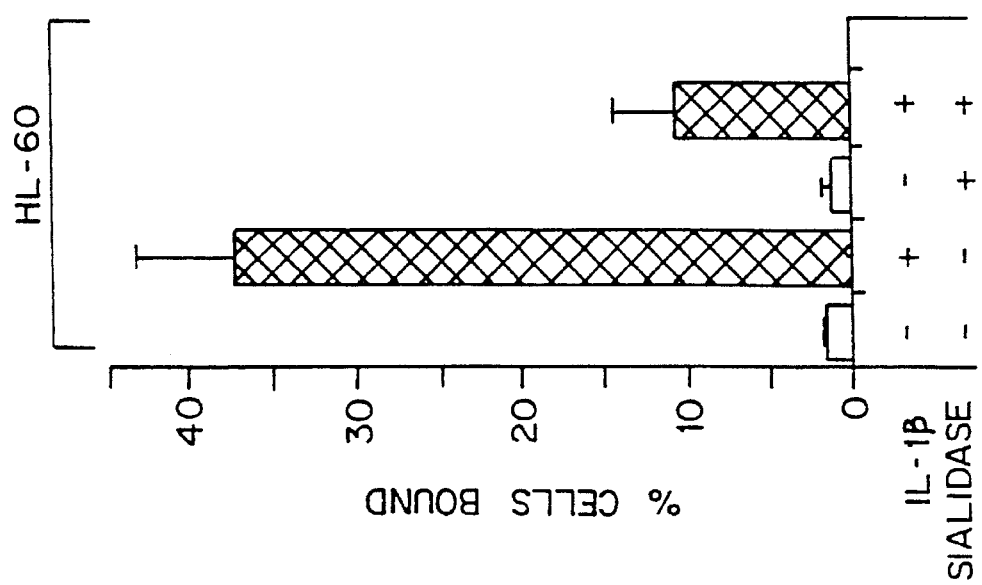
Figure 5:
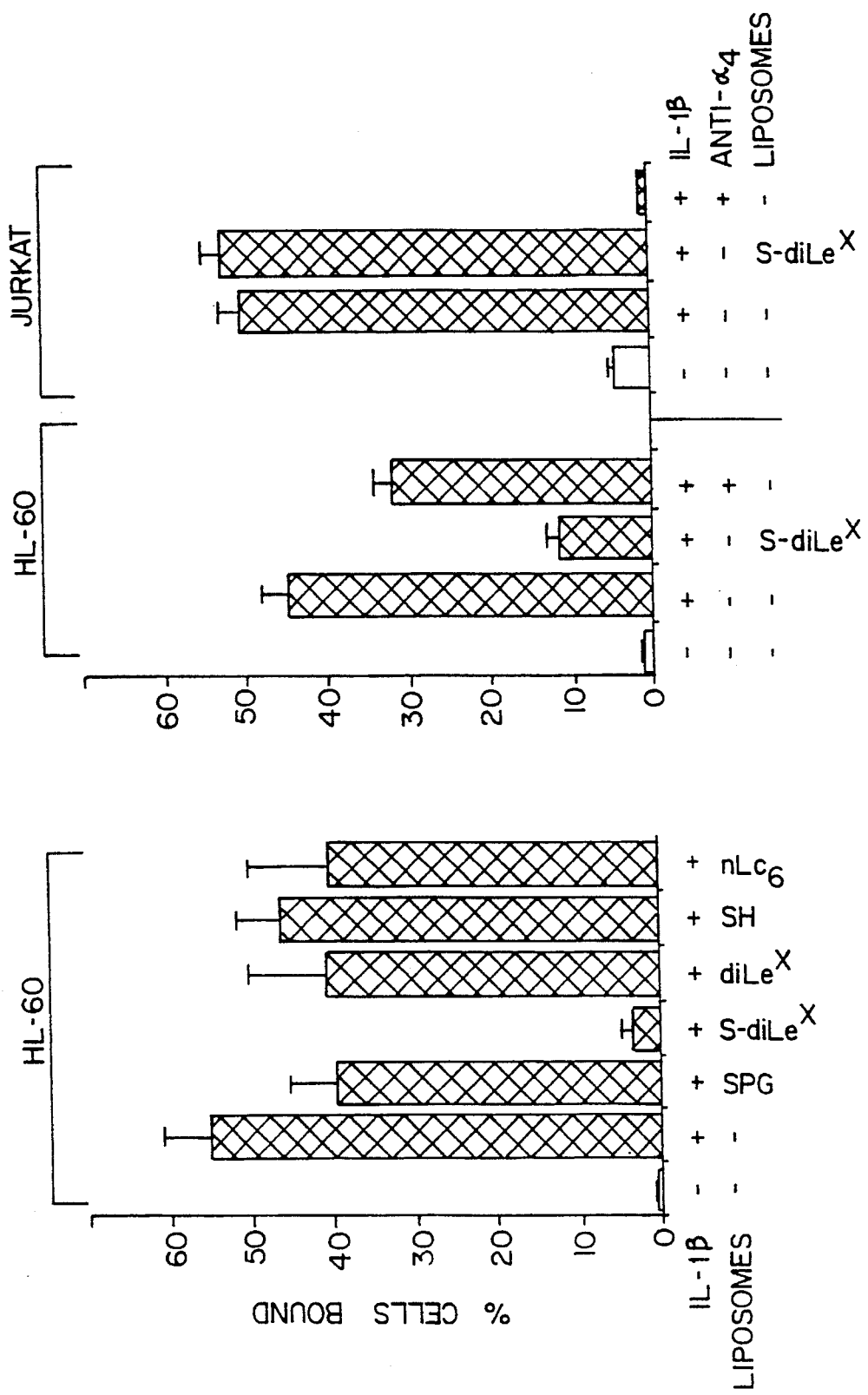
FIGS. 5A and 5B compare the ability of liposomes which contain glycolipids with SLe$^x$, Le$^x$, or similar carbohydrate structures to inhibit the binding of HL-60 cells to activated endothelial cells.
Figure 6:
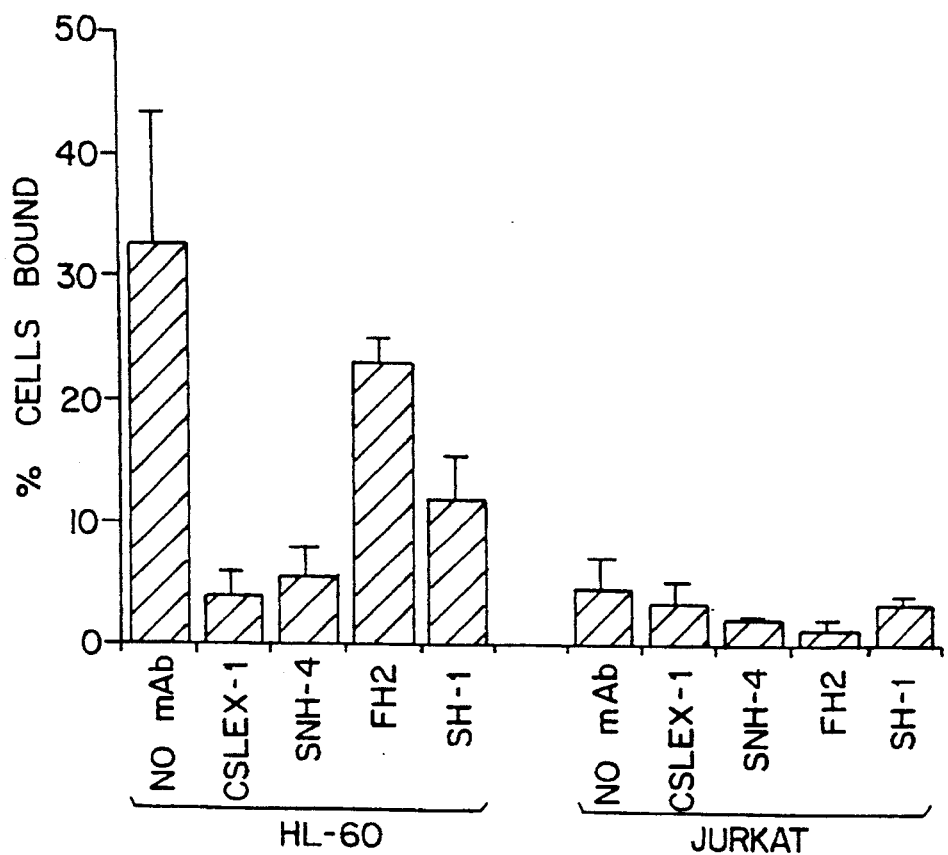
FIG. 6 compares the inhibition of P-Selectin mediated platelet adhesion by monoclonal antibodies specific for SLe$^x$ and Le$^x$ determinants.
Figure 7:
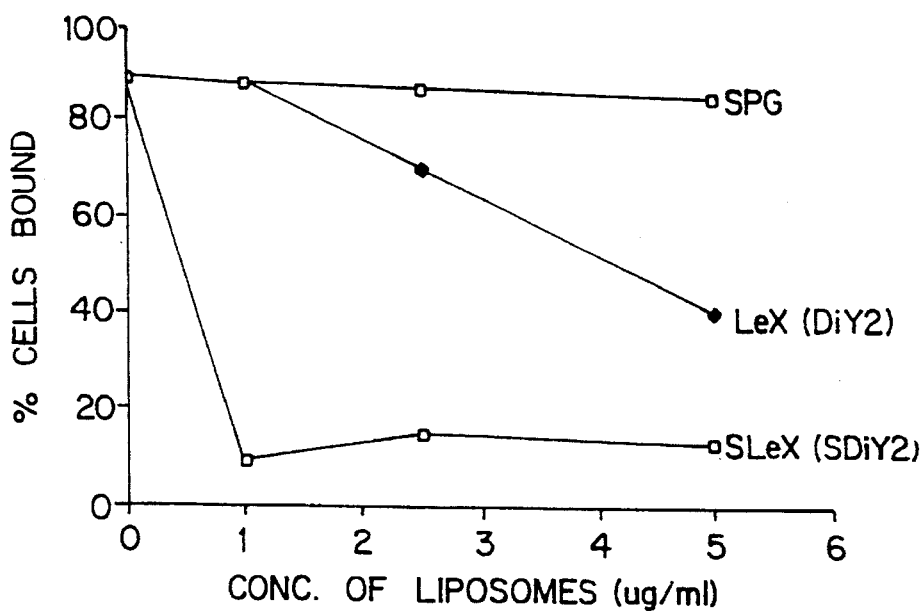
FIG. 7 compares the ability of liposomes which contain glycolipids having SLe$^x$, Le$^x$, or similar carbohydrate structures to inhibit the binding of HL-60 cells to activated platelets.
Figure 8:
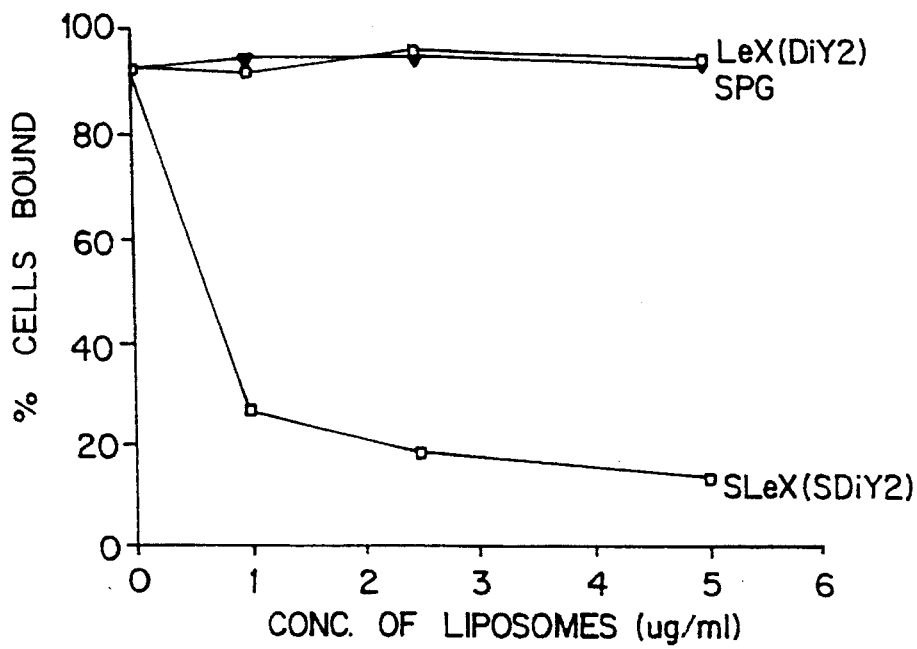
FIG. 8 compares the ability of liposomes which contain glycolipids having SLe$^x$, Le$^x$, or similar carbohydrate structures to inhibit the binding of PMNs to activated platelets.
Figure 9:
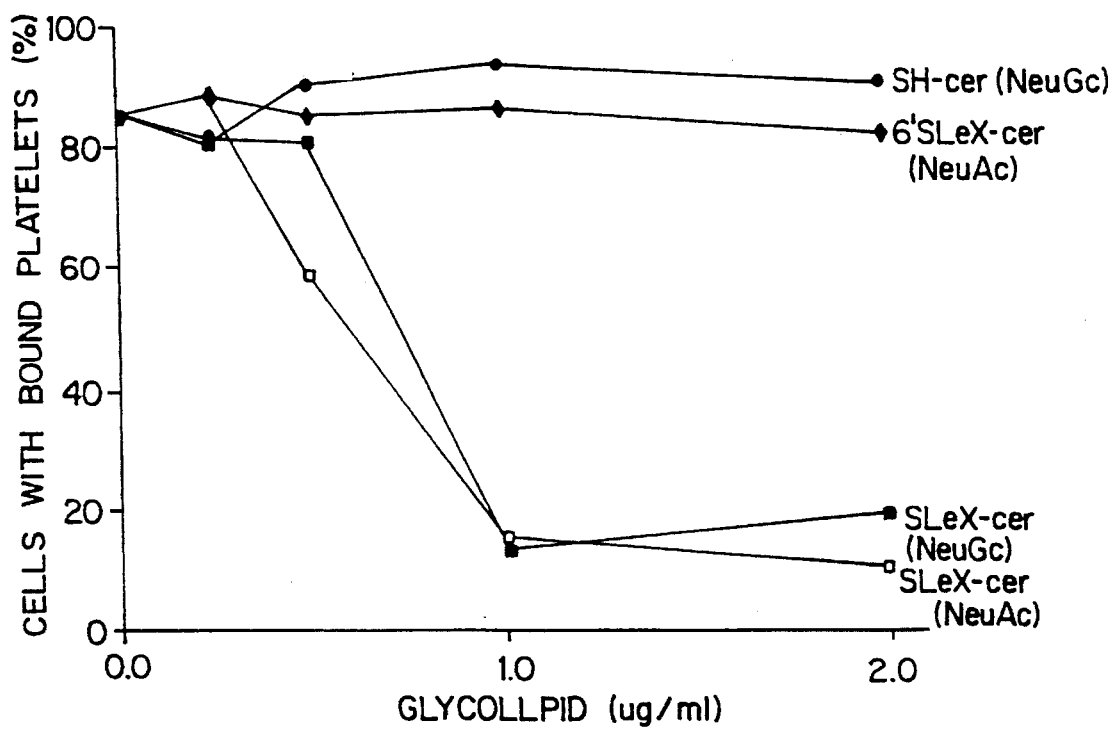
FIG. 9 shows inhibition of P-Selectin mediated adhesion by glycolipids that have either NeuAc or NeuGc as the terminal sialic acid.
Figure 10:
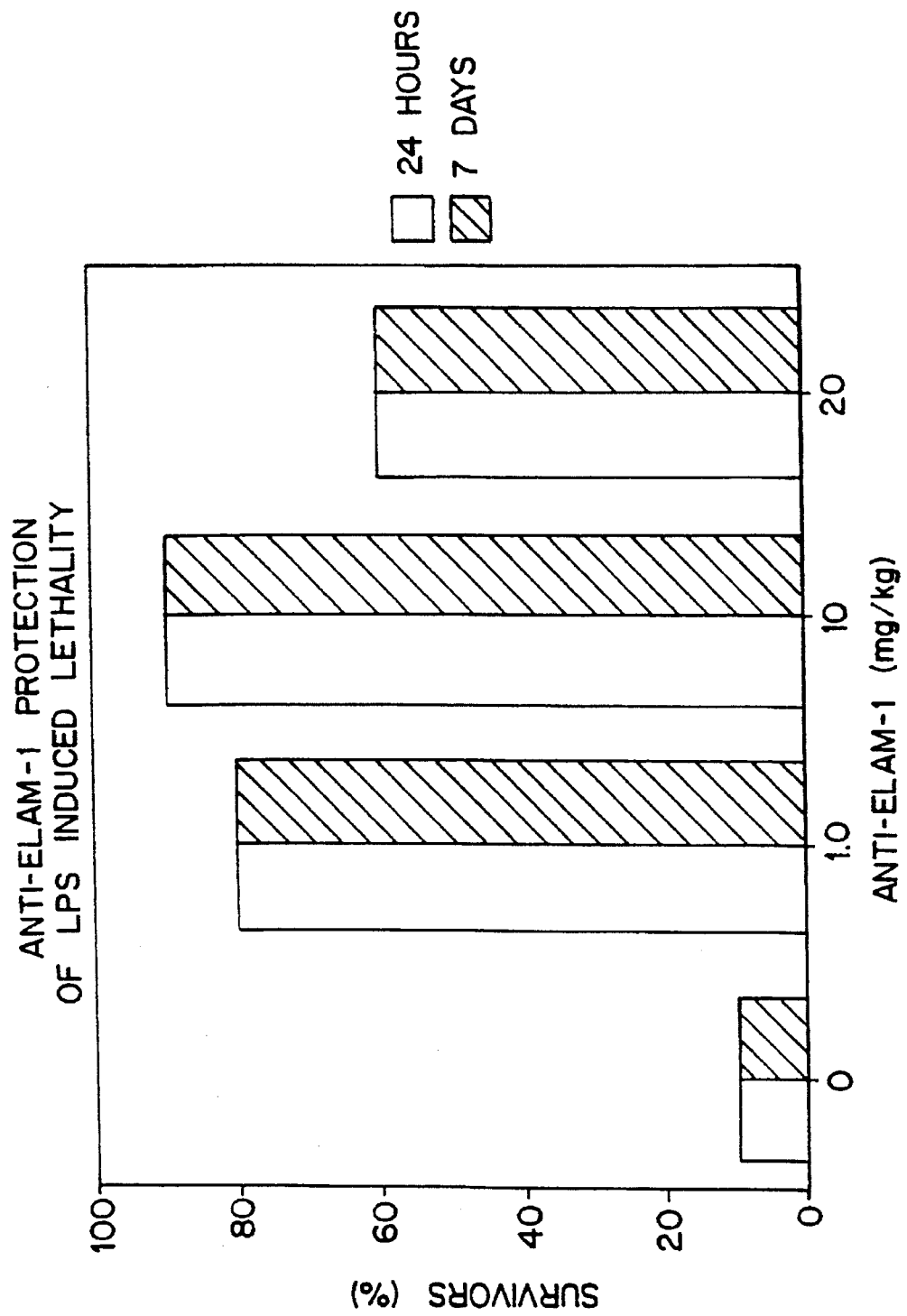
FIG. 10 shows prophylactically administered monoclonal antibodies against E-Selectin prevent lipopolysaccharide induced death in rats.
Figure 11:
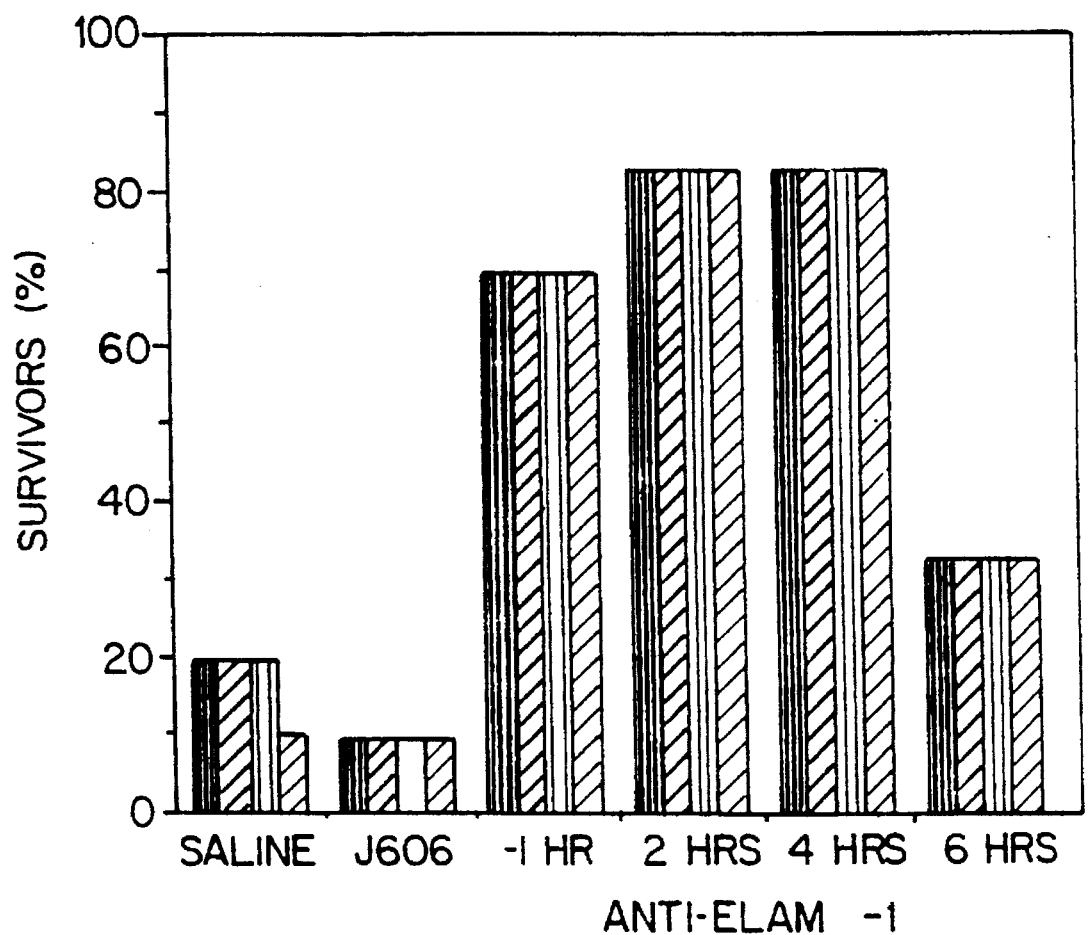
FIG. 11 shows therapeutically administered monoclonal antibodies against E-Selectin prevent lipopolysaccharide induced death in rats.

Compositions and methods are provided for inhibiting inflammatory and other disease responses mediated by cellular adhesion. The present invention also provides compounds (e.g., oligosaccharides, glycoconjugates and monoclonal antibodies) which have the ability to block or inhibit the adhesion of the cells mediated by selectin cell surface receptors. Methods for preparing and screening for such compounds are also provided. Diagnostic and therapeutic uses for the compounds are provided.

A basis of the present invention is the discovery of a carbohydrate moiety recognized by selectin cell surface receptors. As discussed above, selectins, also known as the "LEC-CAM" or selectin family of cell adhesion molecules, are unique glycoproteins expressed on the surface of a variety of cells. For instance, E-Selectin is inducibly expressed on vascular endothelial cells (Bevilacqua et al., supra and Hession et al., *Proc. Natl. Acad. Sci.*, 87:1673–1677 (1990), both of which are incorporated herein by reference). This receptor has been demonstrated to be induced by inflammatory cytokines such as interleukin Iβ (IL-Iβ) and tumor necrosis factor α(TNFα), as well as by bacterial endotoxin (lipopolysaccharide) (see, Bevilacqua et a., *Proc. Nat. Acad. Sci.*, 84:9238–9242 (1987) which is incorporated herein by reference). These compounds act directly on endothelial cells in vitro to substantially augment polymorphonuclear leukocyte (neutrophil), and monocyte adhesion (Bevilacqua et at., *Proc. Natl. Acad. Sci.*, supra).

As discussed above, P-Selectin is a membrane glycoprotein of platelet and endothelial secretory granules (Geng et at., *Nature*, 343:757–760 (1990) which is incorporated herein by reference). Activated platelets which express P-Selectin on their surface are known to bind to monocytes and neutrophils (Jungi et at., *Blood* 67:629–636 (1986)), and also to monocyte-like cell lines, e.g., HL60 and U937 (Jungi et al., supra; Silverstein et at., *J. Clin. Invest.* 79:867–874 (1987)), all of which are incorporated herein by reference. P-Selectin is an alpha granule membrane protein of molecular weight 140,000 that is expressed on the surface of activated platelets upon platelet stimulation and granule secretion (Hsu-Lin et al., *J. Biol. Chem.* 259:9121–9126 (1984); Stenberg et at., *J. Cell Biol*, 101:880–886 (1985); Berman et at., *J. Clin. Invest.* 78:130–137 (1986)). It is also found in megakaryocytes (Beckstead et at., *Blood* 67:285–293 (1986)), and in endothelial cells (McEver et at., *Blood* 70:355a (1987)) within the Weibel-Palade bodies (Bonfanti et al., *Blood* 73:1109–1112 (1989)). Furie et at. U.S. Pat. No. 4,783,330, describe monoclonal antibodies reactive with P-Selectin.

A third selectin receptor is the lymphocyte homing receptor, MEL-14 antigen or LAM-1 (Gallatin et at., *Nature* 304:30–34 (1983); Siegellman et at., *Science*, 243:1165–1172 (1989); Rosen, *Cell Biology*, 1:913–919 (1989); and Lasky et al. *Cell* 56:1045–1055 (1989) all of which are incorporated herein by reference). In addition to lymphocyte homing, MEL-14 antigen/LAM-1 is believed to function early in neutrophil binding to the endothelium.

The structure and function of selectin receptors has been elucidated by cloning and expression of full length cDNA encoding each of the above receptors (see, e.g., Bevilacqua et at., *Science*, supra, (E-Selectin), Geng et at., supra, (GMP 140), and Lasky et al., supra, (MEL-14 antigen)). The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263:9557–9560 (1988) (which is incorporated herein by reference) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

Since selectin receptors comprise a lectin-like domain, the specificity of the molecules is likely to be based on protein-carbohydrate interactions. Evidence provided here indicates that a sialylated, fucosylated N-acetyllactosamine unit of the Lewis X antigen, designated here as SLe$^x$, is a moiety recognized by the lectin region of the selectin receptor. In particular, the evidence shows recognition of this moiety by both E-Selectin and P-Selectin. Compounds of the present invention comprise this fucosylated, sialylated N-acetyllactosamine unit in a variety of configurations.

Selective binding as used herein refers to specific recognition by one molecule (typically referred to as a receptor) of another molecule (typically referred to as a ligand) by the spatial or polar organization of a determinant site on the second molecule. Selective binding between the two molecules occurs where affinity is sufficiently strong. Binding affinity is typically represented by the affinity constant (Ka) for equilibrium concentrations of associated and disassociated configurations, i.e., Ka=[R-L]/[R][L] where [R], [L], and [R-L] are the concentrations at equilibrium of the receptor (R), ligand (L) and receptor-ligand complex (R-L), respectively.

The specific binding interactions of the receptor and ligand molecules typically include reversible noncovalent associations such as electrostatic attraction, Van der Waals forces, and hydrogen bonds. See generally, Stryer, *Biochemistry* (W.H. Freeman and Company, N.Y. 3rd Ed. 1988), which is incorporated herein by reference. Examples of selective binding interactions include antibody-antigen recognition, enzyme-substrate recognition, and the like.

The nomenclature used to describe the oligosaccharide moieties of the present invention follows the conventional nomenclature. Standard abbreviations for individual monosaccharides are used. For instance, 2-N-acetylglucosamine is represented by GlcNAc, fucose is Fuc, galactose is Gal, and glucose is Glc. Two sialic acids which may be present on the oligosaccharides of the present invention are 5-N-acetylneuraminic acid (NeuAc) and 5-N-glycolyl-neuraminic acid (NeuGc). Unless otherwise indicated, all sugars except fucose (L-isomer) are D-isomers in the cyclic configuration (e.g., pyranose or furanose). The two anomers of the cyclic forms are represented by α and β.

The monosaccharides are generally linked by glycosidic bonds to form oligo- and polysaccharides. The orientation of the bond with respect to the plane of the rings is indicated by α and β. The particular carbon atoms that form the bond between the two monosaccharides are also noted. Thus, a β glycosidic bond between C-1 of galactose and C-4 of glucose is represented by Galβ1,4Glc. For the D-sugars (e.g., D-GlcNAc, D-Gal, and D-NeuAc) the designation α means that, when the sugars are represented by Haworth projection drawings (as described in Stryer, supra.), the hydroxyl attached to C-1 (C-2 in NeuAc) is below the plane of the ring and β is above the ring. In the case of L-fucose, the α designation means the hydroxyl is above the ring and β means it is below, again when the sugar is represented by Haworth projection drawings.

The present invention provides a variety of compounds comprising selectin-binding carbohydrate moieties. The selectin-binding moieties of the invention have the general formula:

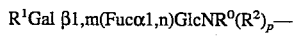

in which $R_0$ is $(C_1-C^8$ alkyl)carbonyl, $(C_1-C_8$ alkoxy)carbonyl, or $(C_2-C_9$ alkenyloxy)carbonyl, $R^1$ is an oligosaccharide or a group having the formula

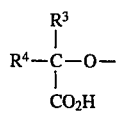

$R^3$ and $R^4$ may be the same or different and may be H, $C_1-C_8$ alkyl, hydroxy-($C_1-C_8$ alkyl), aryl-($C_1-C_8$alkyl), or ($C_1-C_8$ alkoxy)-($C_1-C_8$ alkyl), substituted or unsubstituted. $R^2$ may be H, $C_1-C_8$ alkyl, hydroxy-($C_1-C_8$ alkyl), aryl-($C_1-C_8$ alkyl), ($C_1-C_8$ alkyl)-aryl, alkylthio, α1,2Man, α1,6GalNAc, β1,3Galβ1,4Glc, α1,2Man—$R^8$, α1,6GalNAc—$R^8$, and β1,3Gal—$R^8$. $R^8$ may be H, $C_1-C_8$ alkyl, $C_1-C_8$ alkoxy, hydroxy-($C_1-C_8$ alkyl), aryl-($C_1-C_8$ alkyl), ($C_1-C_8$ alkyl)-aryl, or alkylthio. In the formula, m and n are integers and may be either 3 or 4; p may be zero or 1.

The substituted groups mentioned above may be substituted by hydroxy, hydroxy($C_1-C_4$ alkyl), polyhydroxy($C_1-C_4$ alkyl), alkanoamido, or hydroxyalknoamido substituents. Preferred substituents include hydroxy, polyhydroxy($C_3$ alkyl), acetamido and hydroxyacetamido. A substituted radical may have more than one substitution, which may be the same or different.

For embodiments in which $R^1$ is an oligosaccharide, the oligosaccharide is preferably a trisaccharide. Preferred trisaccharides include NeuAcα2,3Galβ1,4GlcNAcβ1,3 or NeuGcα2,3Galβ1,4GlcNAcβ1,3.

For embodiments in which $R^1$ is the group having the formula

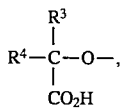

$R^3$ and $R^4$ preferably form a single radical having the formula

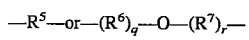

in which $R^5$ is $C_3$–$C_7$ divalent alkyl, substituted or unsubstituted, $R^6$ and $R^7$ are the same or different and are $C_1$–$C_6$ divalent alkyl, substituted or unsubstituted. In the formula, q and r are integers which may be the same or different and are either zero or 1. The sum of q and r is always at least 1.

A more preferred structure for a single radical formed by $R^3$ and $R^4$ is one having the formula

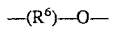

in which $R^6$ is $C_3$–$C_4$ divalent alkyl, substituted or unsubstituted. For instance, $R^6$ may have the formula —$CH_2$—$CH_2$—$CH_2$—$CH_2$—, preferably substituted. The radical can be substituted with hydroxy, polyhydroxy($C_3$ alkyl), and substituted or unsubstituted alkanoamido groups, such as acetamido or hydroxyacetamido. The substituted structure will typically form a monosaccharide, preferably a sialic acid such as NeuAc or NeuGc linked α2,3 to the Gal residue.

In the general formula, above, both m and n are integers and can be either 3 or 4. Thus, in one set of structures Gal is linked β1,4 and Fuc is linked α1,3 to GlcNAc. This formula includes the $SLe^x$ tetrasaccharide. SLex has the formula NeuAcα2,3Galβ1,4(Fucα1,3)GlcNAcβ1—. The data presented below demonstrates that this structure is selectively recognized by LECCAM-bearing cells.

A related set of structures included in the general formula are those in which Gal is linked β1,3 and Fuc is linked α1,4. For instance, the tetrasaccharide, NeuAcα2,3Galβ1,3(Fucα1,4)GlcNAcβ1—, termed here $SLe^a$, is recognized by selectin receptors. See, Berg et at. *J. Biol. Chem.*, 266:14869–14872 (1991). In particular, Berg et al. showed that cells transformed with E-Selectin cDNA selectively bound neoglycoproteins comprising $SLe^a$.

The abbreviation "Alloc" stands for allyloxycarbonyl.

The term "alkyl" as used herein means a branched or unbranched, saturated or unsaturated, monovalent or divalent, hydrocarbon radical having from 1 to 20 carbons, including lower alkyls of 1–8 carbons such as methyl, ethyl, n-propyl, butyl, n-hexyl, and the like, cycloalkyls (3–7 carbons), cycloalkylmethyls (4–8 carbons), and arylalkyls.

The term "aryl" refers to a radical derived from an aromatic hydrocarbon by the removal of one atom, e.g., phenyl from benzene. The aromatic hydrocarbon may have more than one unsaturated carbon ring, e.g., naphthyl.

The term "alkoxy" refers to alkyl radicals attached to the remainder of the molecule by an oxygen, e.g., ethoxy, methoxy, or n-propoxy.

The term "alkylthio" refers to alkyl radicals attached to the remainder of the molecule by a sulfur.

An "alkanoamido" radical has the general formula —NH—CO—($C_1$–$C_6$ alkyl) and may or may not be substituted. If substituted, the substituent is typically hydroxyl. The term specifically includes two preferred structures, acetamido, —NH—CO—$CH_3$, and hydroxyacetamido, —NH—CO—$CH_2$—OH.

The term "heterocyclic compounds" refers to ring compounds having three or more atoms in which at least one of the atoms is other than carbon (e.g., N, O, S, Se, P, or As). Examples of such compounds include furans (including the furanose form of pentoses, such as fucose), pyrans (including the pyranose form of hexoses, such as glucose and galactose) pyrimidines, purines, pyrazines and the like.

The term "oligo" refers to a polymeric molecule consisting of 2 to approximately 10 residues, for example, amino acids (oligopeptide), monosaccharides(oligosaccharide), and nucleic acids (oligonucleotide). The term "poly" refers to a polymeric molecule comprising greater than about 10 residues. The sialic acid residue in the structures described above may be in different forms, so long as selectin binding is not significantly affected. Typically, the sialic acid is 5-N-acetylneuraminic acid, (NeuAc) or 5-N-glcolylneuraminic acid (NeuGc). Other sialic acids may be used in their place, however. For a review of different forms of sialic acid suitable in the present invention see generally, R. Schauer, *Methods in Enzymology*, 50: 64–89 (1987), and Schaur, *Advances in Carbohydrate Chemistry and Biochemistry*, 40: 131–234; both of which are incorporated by reference. As demonstrated in Example IX, below, the affinity for selectin receptors is the same if the oligosaccharide terminates in NeuAc or NeuGc. The term "$SLe^x$" as used herein refers to the minimal tetrasaccharide unit, NeuAcα2,3Galβ1,4(Fucα1,3)GlcNAcβ1,3—. The skilled artisan, however, will appreciate that the NeuAc may replaced by NeuGc or other equivalent forms of sialic acid. Structures illustrated herein which show the sialic acid residue as NeuAc are understood to include these other forms, in particular NeuGc.

Having identified carbohydrate ligands that mediate leukocyte-endothelial and leukocyte-platelet cell adhesion, compounds comprising $SLe^x$ and related structures can be purified or synthesized de novo. As detailed below, the present invention provides a variety of compounds comprising the selectin-binding moieties of the present invention. For instance, biomolecules can be used as the moiety-bearing compound. Biomolecules as defined here include but are not limited to biologically significant molecules such as amino acids (and their mimetics), oligopeptides, proteins (e.g., glycoproteins and protein hormones), fatty acids, lipids (e.g., glycolipids, phospholipids, sphingolipids and gangliosides), steroid hormones, oligosaccharides, polysaccharides, and nucleic acids (e.g., deoxyribonucleic acids and ribonucleic acids). These compounds can be purified and/or synthesized according to standard techniques known to the skilled artisan. In addition, a wide variety of compounds bearing the moiety may be synthesized de novo as described below.

All the compounds mentioned above can be used for a variety of purposes, including, for example, competitive inhibition of the binding of $SLe^x$-bearing cells to cells that express the selectin receptors. By binding of the compounds of the invention to a cell surface selectin, interaction of the selectin with the native $SLe^x$ ligand on migrating cells will be prevented, interfering with normal and pathological binding of leukocytes and other cells to the endothelium or platelets. Thus, compounds that contain one or more selectin-binding moieties can serve as effective inhibitors of, for instance, inflammation, atherosclerosis, clotting and other endothelial or platelet-mediated pathologies.

Figure 12A:
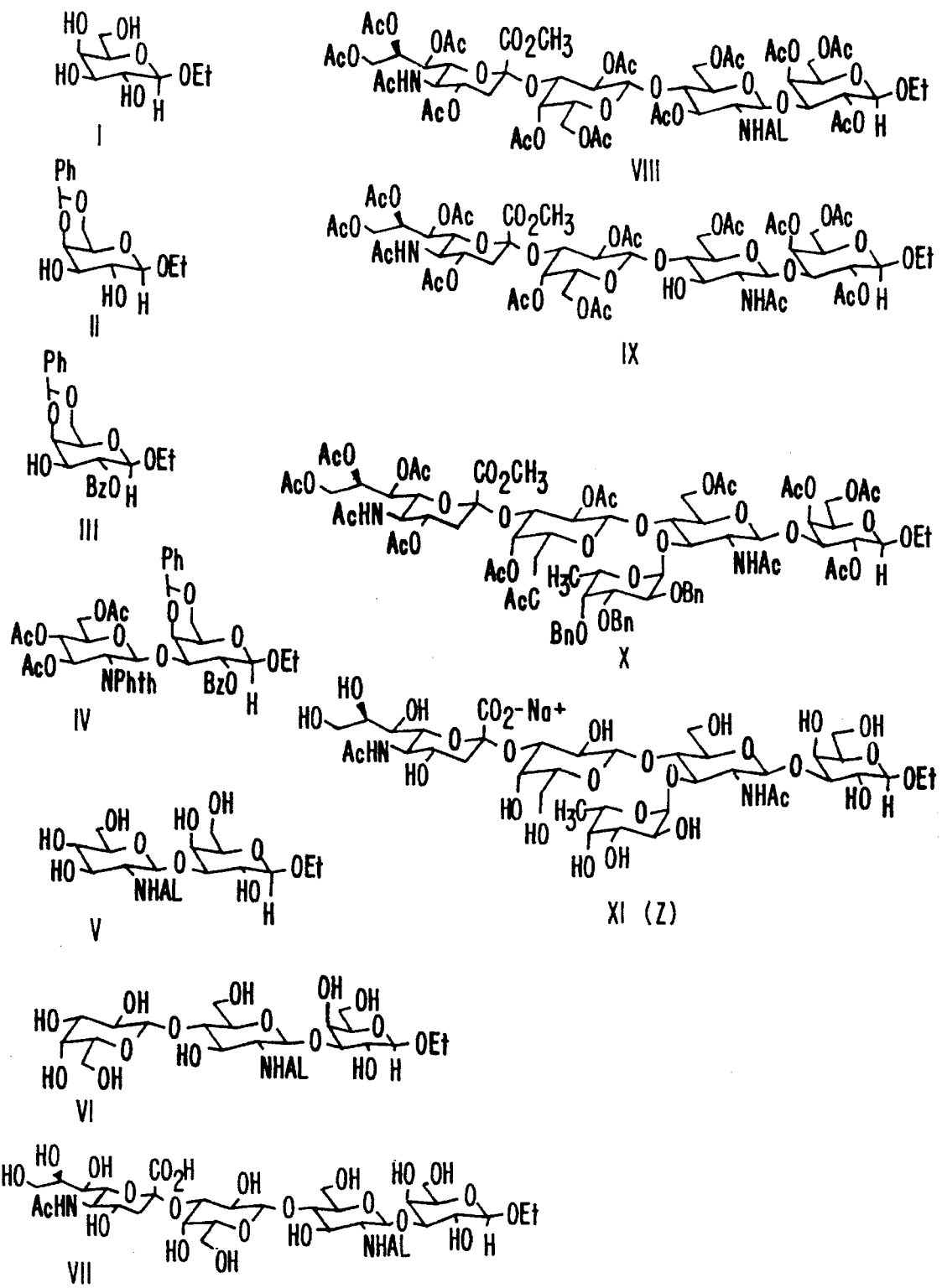
FIGS. 12A and 12B show intermediate compounds in the synthesis of Z (12A) and structure of related analogs (12B).
Figures 1, 12B:
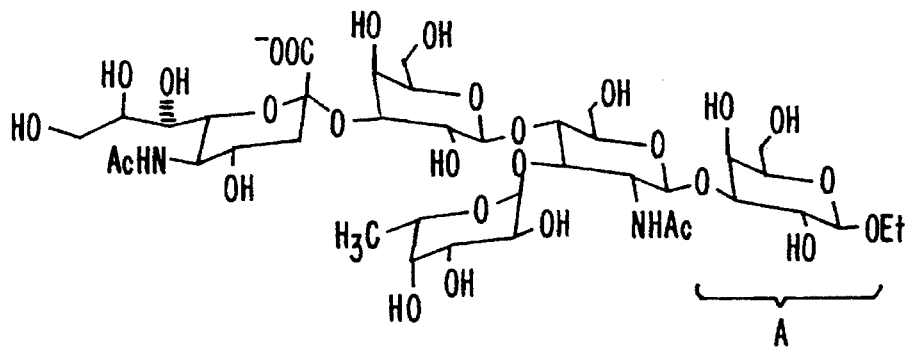
Figure 14:
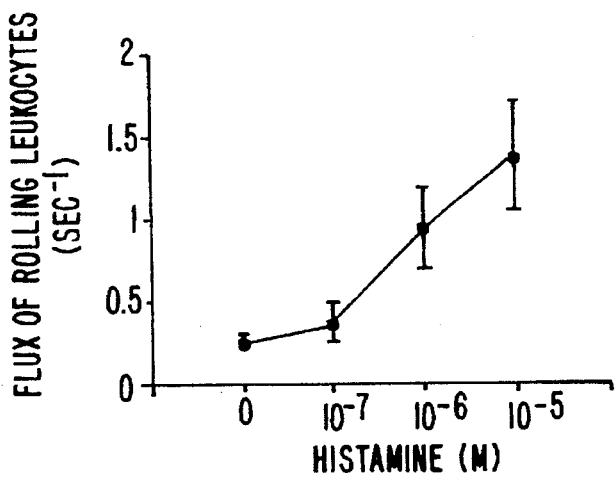
FIG. 14 summarizes the changes in the flux of rolling leukocytes (Panel A), leukocyte rolling velocity (Panel B), and number of rolling leukocytes (Panel C) induced by different concentrations of histamine.
Figure 14:
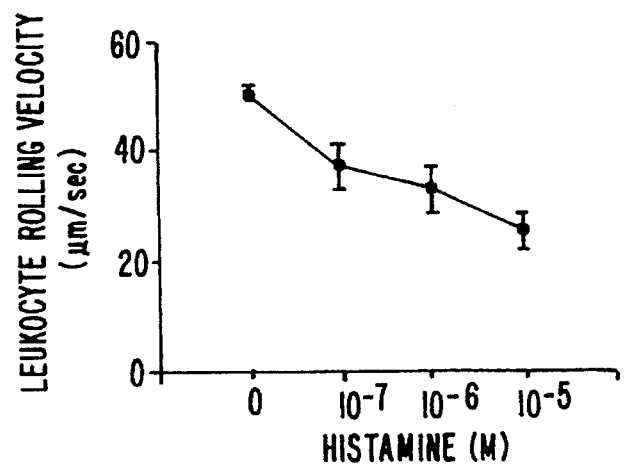
Figure 14:
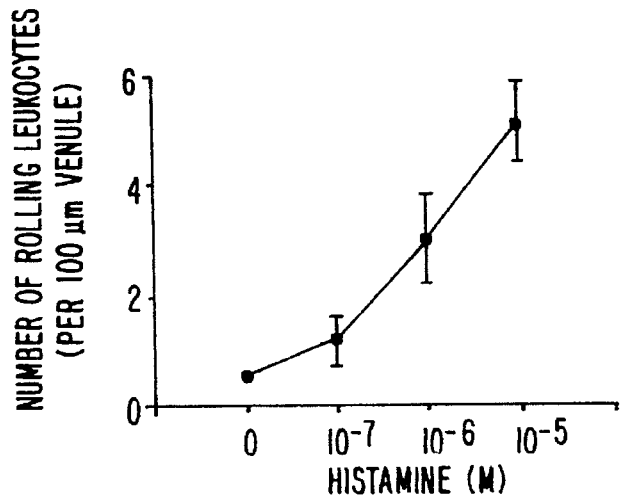
Figure 15:
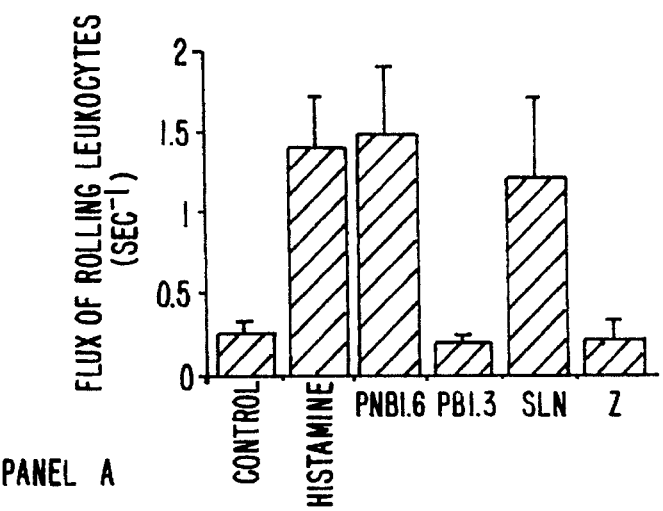
FIG. 15 shows that a blocking monoclonal antibody to P-selectin (PB1.3) prevented recruitment of rolling leukocytes while a second isotype matched nonblocking P-selectin antibody, which does not cross react with rat P-selectin (PNB1.6), had no effect. Similarly, Z inhibited leukocyte rolling, while SLN had no effect.
Figure 15:
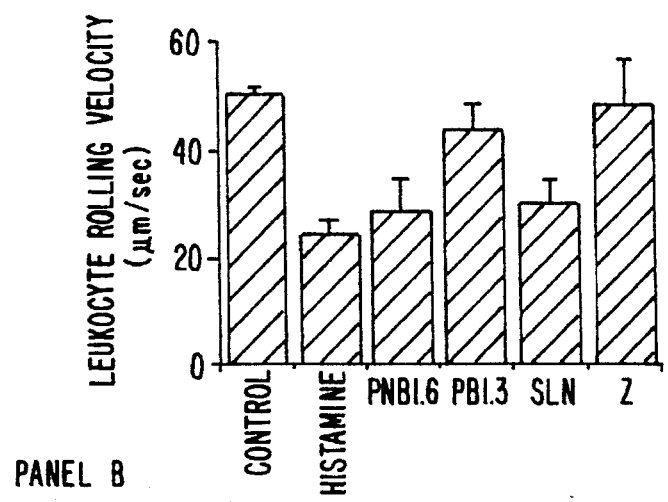
Figure 15:
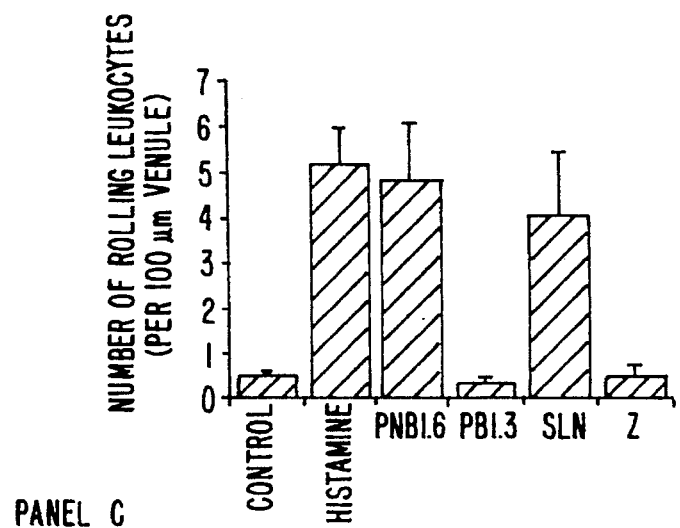
Figure 16:
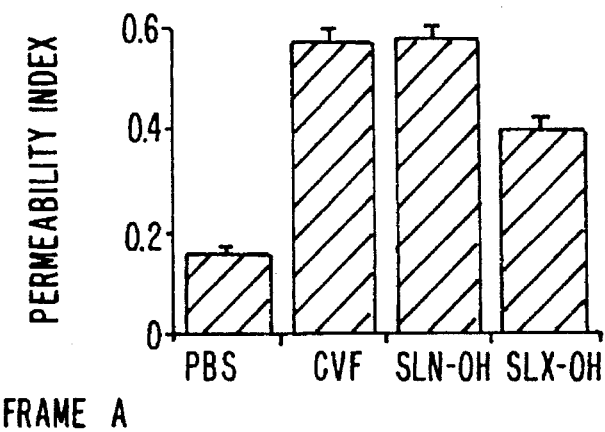
FIG. 16 shows changes in pulmonary vascular permeability (panel A), hemorrhage (panel B) and neutrophil accumulation (panel C) 30 minutes following injection of CVF. Groups of rats were pretreated with either vehicle, SLN-OH (0.6 mg/Kg), or with SLX-OH (0.6 mg/Kg) 5 minutes prior to administration of either CVF or PBS. Each bar represents the mean of 6 animals and vertical lines represent the standard error of the mean.
Figure 16:
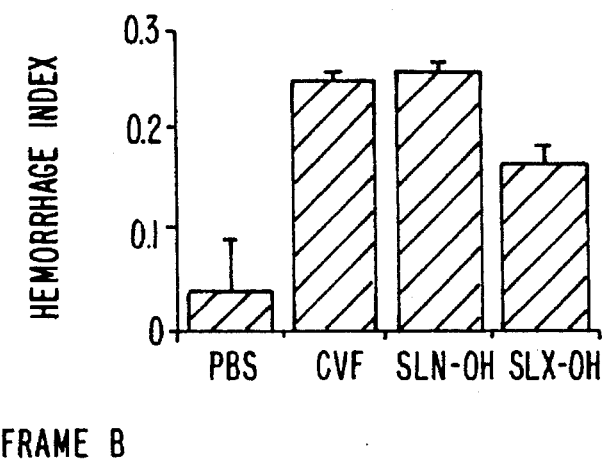
Figure 16:
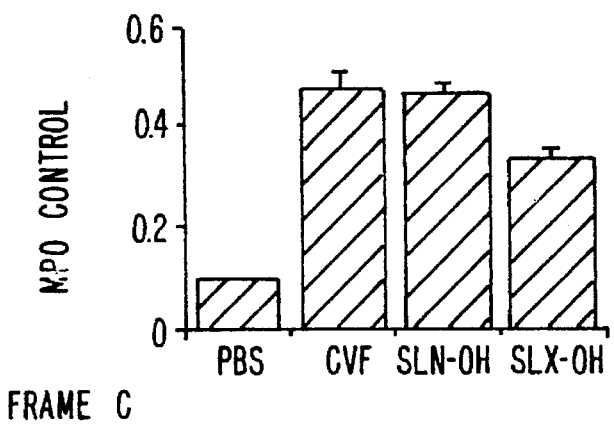
Figure 17:
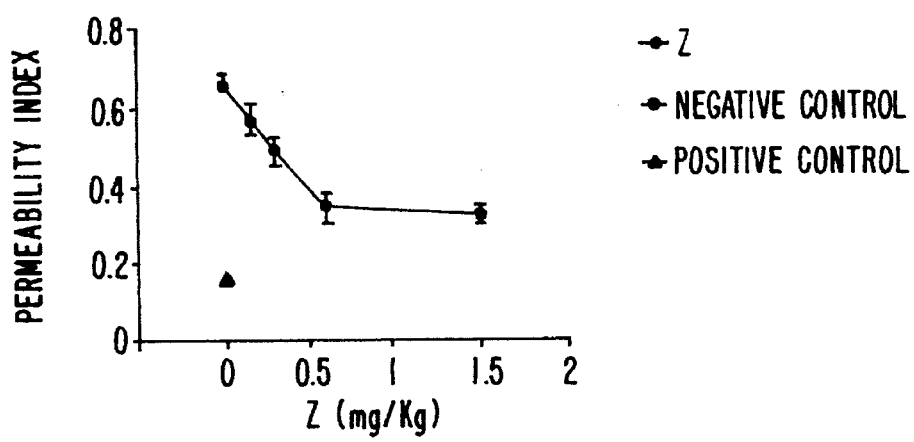
FIG. 17 shows changes in pulmonary vascular permeability (panel A), hemorrhage (panel B) and neutrophil accumulation (panel C) were determined 30 minutes following injection of CVF. Groups of rats were pretreated with either vehicle or Z at the indicated doses 5 minutes prior to administration of CVF or PBS. Each point represents the mean of 6 animals and vertical lines represent the standard error of the mean.
Figure 17:
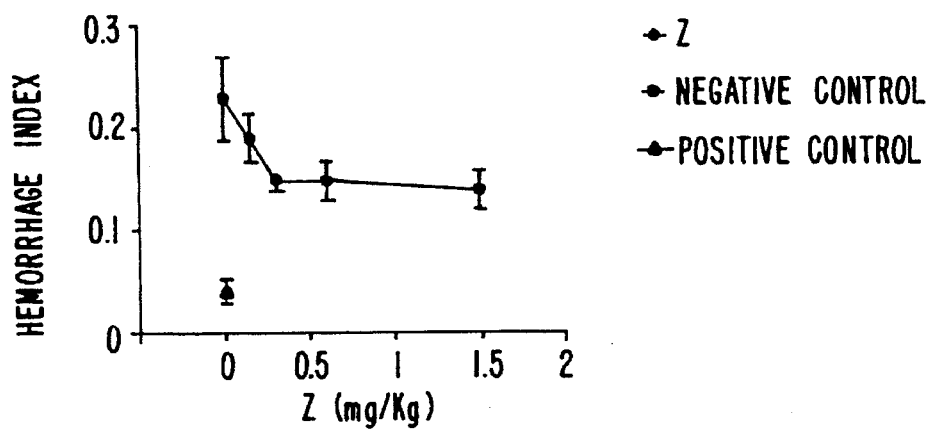
Figure 17:
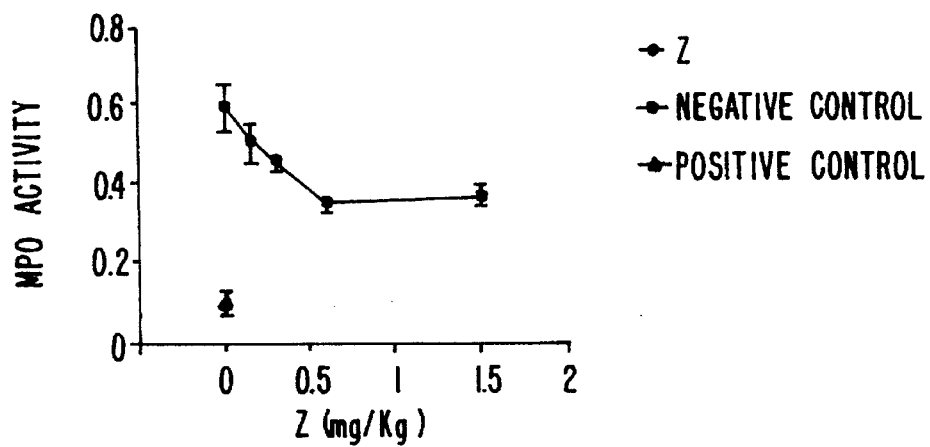
Figure 18:
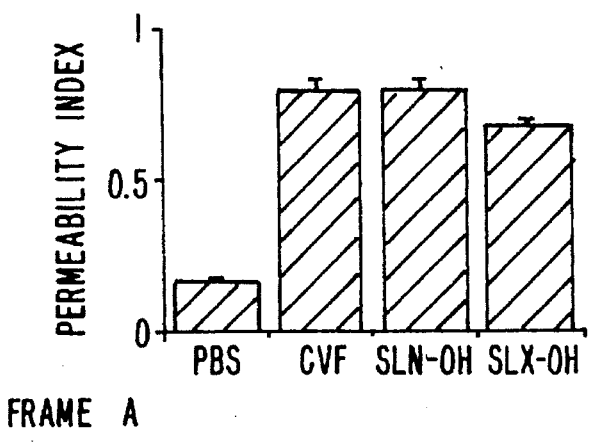
FIG. 18 shows changes in pulmonary vascular permeability (panel A), hemorrhage (panel B) and neutrophil accumulation (panel C) were determined 4 hours following initiation of inflammation by intrapulmonary deposition of IgG immune complexes. Groups of rats were dosed with either vehicle, SLN-OH (100 µg), or with SLX-OH (100 µg) 2.5, 3 and 3.5 hours post induction of inflammation. Each bar represents the mean of 6 animals and vertical lines represent the standard error of the mean.
Figure 18:
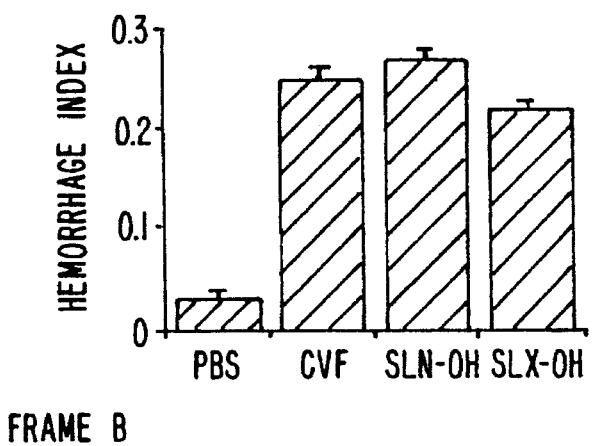
Figure 18:
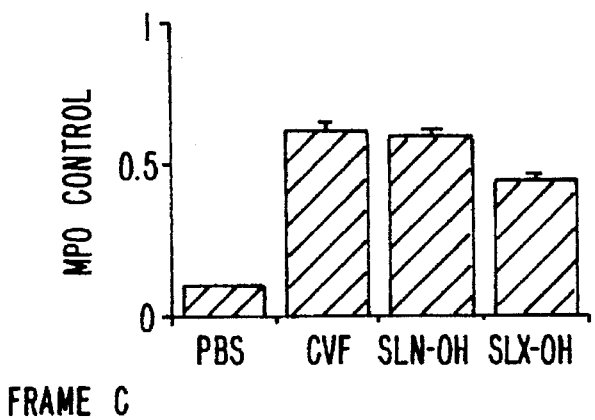
Figure 19:
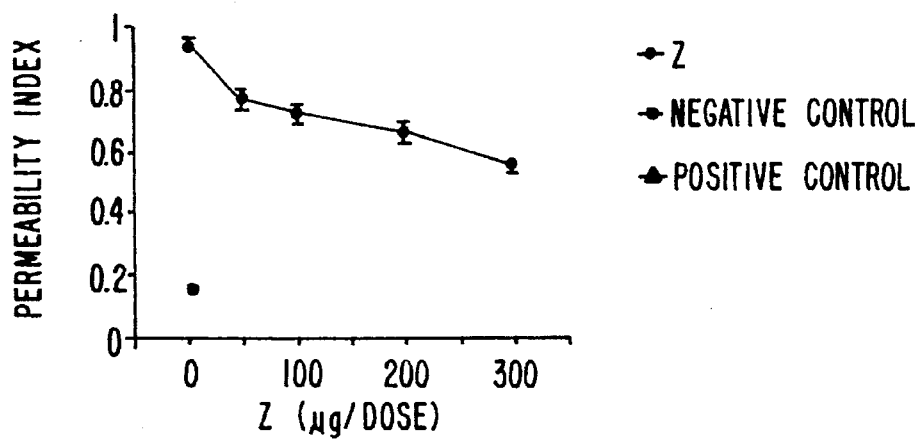
FIG. 19 shows changes in pulmonary vascular permeability (panel A), hemorrhage (panel B) and neutrophil accumulation (panel C) were determined 4 hours following initiation of inflammation by intrapulmonary deposition of IgG immune complexes. Groups of rats were dosed with either vehicle, SLN-OH, or with Z at the indicated doses 2.5, 3 and 3.5 hours post induction of inflammation. Each point represents the mean of 6 animals and vertical lines represent the standard error of the mean.
Figure 19:
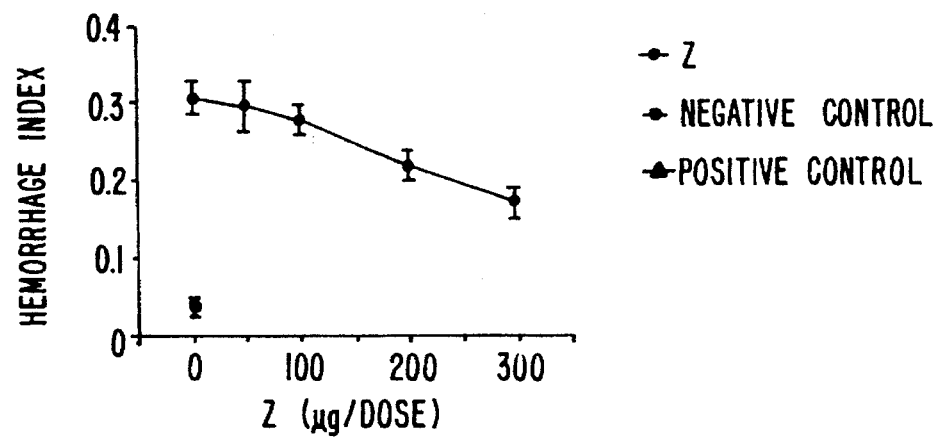
Figure 19:
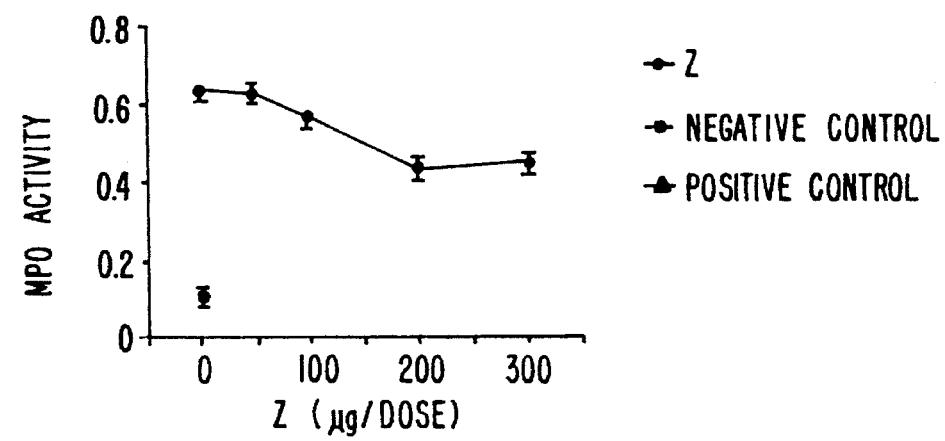
Figure 20:
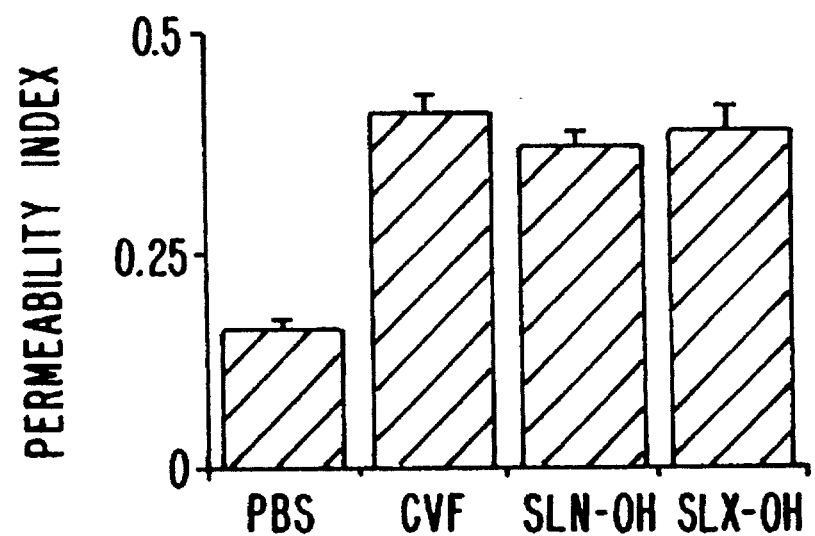
FIG. 20 shows changes in pulmonary vascular permeability (panel A) and hemorrhage (panel B) were determined 4 hours following initiation of inflammation by intrapulmonary deposition of IgA immune complexes. Groups of rats were dosed with either vehicle, SLN-OH (100 µg), or with SLX-OH (100 µg) 2.5, 3 and 3.5 hours post induction of inflammation. Each bar represents the mean of 6 animals and vertical lines represent the standard error of the mean.
Figure 20:
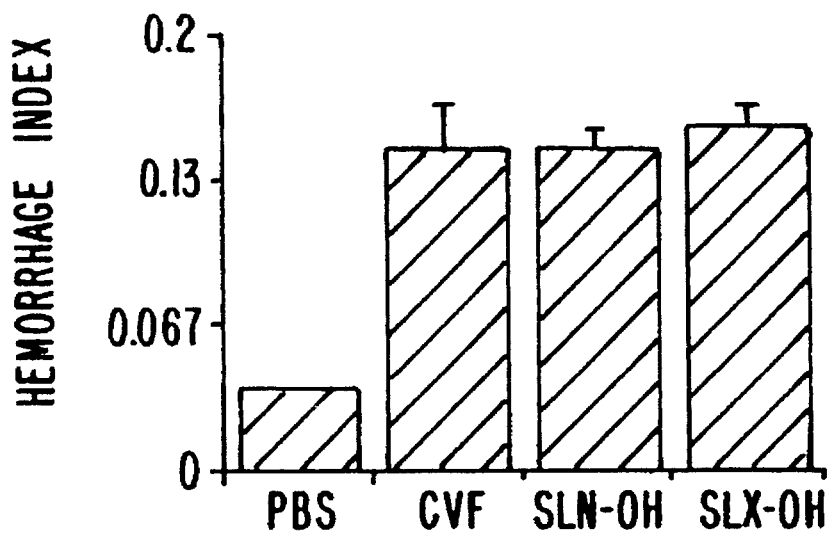
Figure 21:
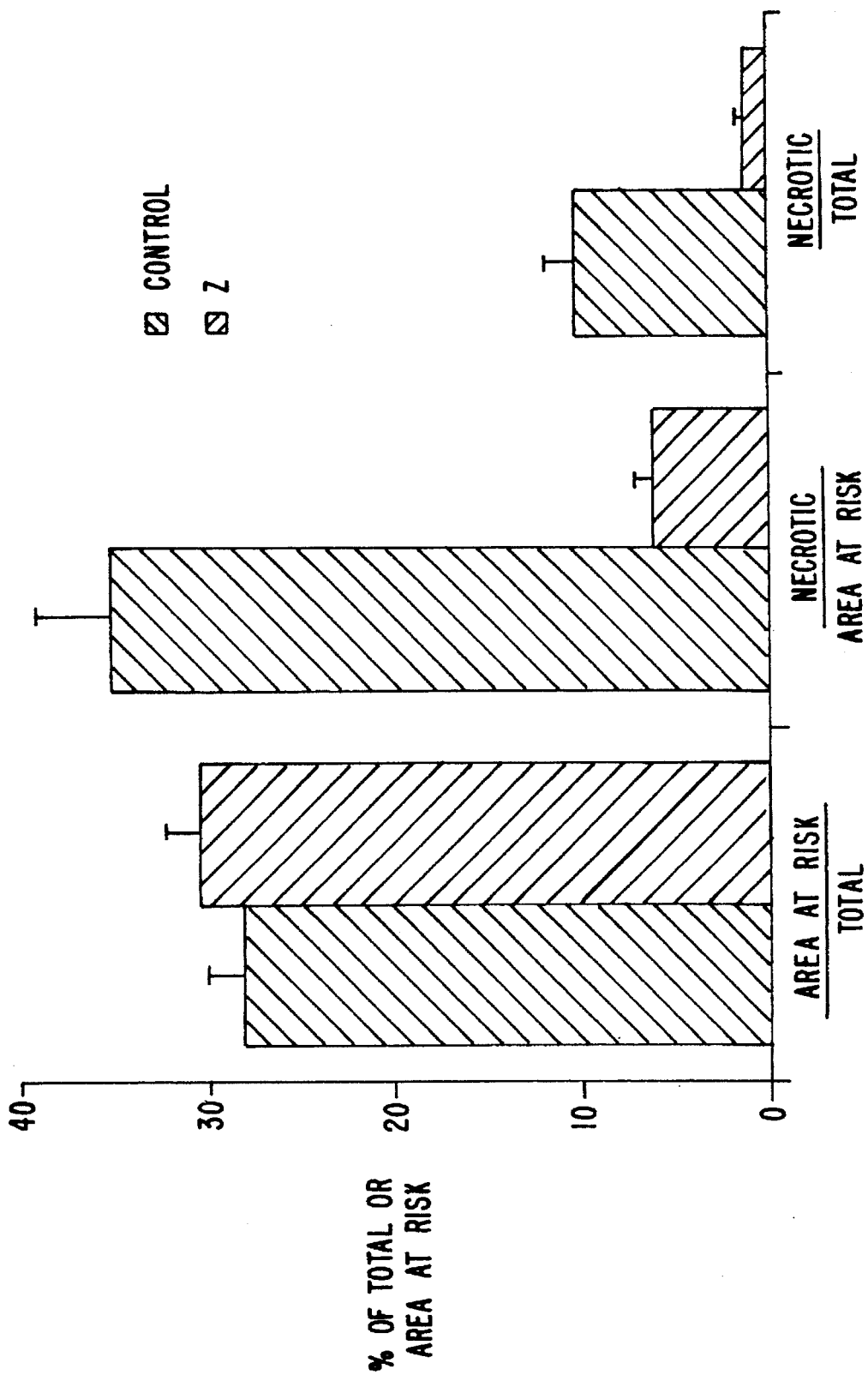
FIG. 21 shows the effect of Z on ischemia reperfurion induced myocardial necrosis in cat.

Evidence provided below shows that a pentasaccharide comprising the formula: NeuAcα2,3Galβ1,4(Fucα1,3)GlcNAcβ1,3Galβ— is a minimal structure having substantially more inhibitory effect than the tetrasaccharide. A preferred pentasaccharide is Z (NeuAcα2,3Galβ1,4(Fucα1,3)GlcNAcβ1,3Galβ—$OCH_2CH_3$). Other preferred oligosaccharides are shown in FIG. 12B.

The oligosaccharide moiety of the present invention preferably terminates in a sialic acid residue. In certain embodiments the sialic acid residue can be further linked to other saccharide residues, such as a second sialic acid in an α2,8 linkage.

Alternatively, the terminal sialic acid residue may be replaced by a variety of radicals. Thus, certain selectin binding moieties of the present invention have the general formula: $R^1$-NeuAcα2,3Galβ1,4GlcNAcβ1-, wherein $R^1$ is $R^2R^3C(CO_2H)$—, wherein $R^2$ and $R^3$ are the same or different and are H, lower alkyl (C1–C8), hydroxyl lower alkyl (C1–C8), arylalkyl, alkoxylalkyl. In addition, $R^2$ and $R^3$ may be connected to form a 4–8 membered carbocyclic or heterocyclic ring.

Compounds containing $SLe^x$ and related structures can be obtained from the cell surface glycoproteins or glycolipids from a number of cells. For instance, the $SLe^x$ antigen is present on N-linked carbohydrate groups of the cell surface glycoproteins of LEC11 cells, a glycosylation mutant of chinese hamster ovary (CHO) cells. LEC11 expresses this unique glycopeptide which contains a terminal structure bearing both sialic acid and fucose in the $SLe^x$ sequence:

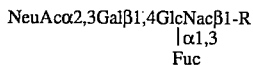

where R is:

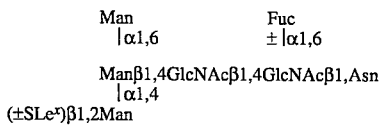

(See, Stanley et at., J. Biol. Chem, 263:11374 (1988), which is incorporated herein by reference.) Using the procedure described below, it was demonstrated that the LEC11 mutant bound to activated human vascular endothelial cells. Neither wild type CHO cells nor other related glycosylation mutant CHO cell lines without the particular glycosylation pattern ($SLe^x$) showed the same level of binding.

Other sources that can be used to obtain the $SLe^x$ unit include any cell that naturally expresses the moiety on glycolipid or glycoprotein carbohydrate groups. Thus, polymorphonuclear neutrophils, lymphocytes, tumor cells or HL-60 cells have been used to purify this unit. Other cells that bind to activated vascular endothelium can also be used as a source from which the ligand may be isolated (see, Symington et al., J, Immunol. 134:2498–2506 (1985), Mizoguchi et al., J. Biol. Chem. 259:11949–11957 (1984), Mizoguchi et al., J. Biol. Chem. 259:11943–11948 (1984), Paietta et al., Cancer Res. 48:280–287 (1988), all of which are incorporated herein by reference).

Compounds containing $SLe^x$ or its mimetics can be prepared from natural sources using methods well known in the art for isolating surface glycoproteins, glycopeptides, oligosaccharides and glycolipids from cells (See, e.g., Gerard, "Purification of glycoproteins" and Thomas et al., "Purification of membrane proteins," both in Guide to Protein Purification, Vol. 182, Methods in Enzymology (Deutscher ed., 1990), which is incorporated herein by reference). For example, LEC11 cells can be used to obtain glycoprotein or glycolipid that contains the $SLe^x$ unit using, for instance, the method described in Stanley et al., supra. Briefly, LEC11 cells are infected with vesicular stomatitis virus. The structural carbohydrate alterations exhibited by LEC11 are then expressed on the N-linked biantennary carbohydrates of the G glycoprotein of the virus. The virus is purified by equilibrium gradient centrifugation, and glycopeptides are purified using proteinase digestion as described by Stanley et al.

Alternatively, the selectin-binding moiety can be synthesized using chemical, enzymatic, or combined chemical and enzymatic strategies. (see, e.g., EPO Publication No. 319, 253, which is incorporated herein by reference.) In a preferred method (Scheme I below), a compound containing one or more N-acetylglucosamine units (GlcNAc-R) can be reacted sequentially with a galactosyltransferase (N-acetylglucosamine β1,4 galactosyltransferase (E.C. 2.4.1.90)), a sialyltransferase (Galβ1,4GlcNAc α2,3 sialyltransferase (E.C. 2.4.99.6)or Galβ1,3GalNAc α2,3 sialyltransferase (E.G. 2.4.99.4)) and a fucosyltransferase (N-acetylglucosaminide α1,3 fucosyltransferase E.C. 2.4.1.152)) to yield the final $SLe^x$-containing structures. In this case, R may be a carrier moiety or an activatable intermediate that will allow attachment to a suitable carrier moiety. Each enzymatic reaction uses the appropriate nucleotide sugar as a donor substrate to generate the following intermediates in the synthesis of $SLe^x$. The glycosyl transfer reactions may optimally be carried out with added alkaline phosphatase (e.g., from calf intestine, CIAP) to consume the nucleoside phosphate byproduct which may inhibit the reaction.

Scheme I

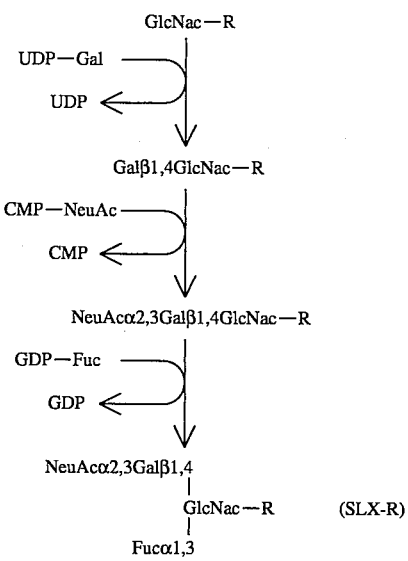

The general conditions for preparative enzymatic synthesis of carbohydrate groups analogous to $SLe^x$ are known (see, e.g., Toone et al., Tetrahedron 45:5365–5422 (1989); Wong et. al., J. Am. Chem. Soc. 104:3542–3544 (1982); Unverzagt et al., J. Am. Chem. Soc. 112:9308–9309 (1990); Prieels et al., J. Biol. Chem. 256:10456–10463 (1981), all of which are incorporated herein by reference). Each of the key enzymatic reactions has been demonstrated (Beyer et al., Adv. Enzymol. 52:23–176 (1981); Toone et al., supra; and Howard et al., J. Biol. Chem. 262:16830–16837 (1981); all of which are incorporated herein by reference). For preparative reactions, the galactosyltransferase and the sialyltransferase(s) are purified from natural sources (Beyer et al., supra, and Weinstein et al., J. Biol. Chem. 257:13835–13844 (1982), which are incorporated herein by reference). Fucosyltransferases may also be purified from natural sources, as generally described in Crawley and Hindsgaul, Carbohyd. Res. 193:249–256 (1989), incorporated by reference herein. The cDNAs of the galactosyltransferase and a sialyltransferase have been cloned (Paulson and Colley, J. Biol. Chem. 264:17615–17618 (1989), which is incorporated herein by reference), allowing the production of soluble recombinant enzymes for large-scale preparative synthesis (Colley et al., J, Biol. Chem. 264:17619–17622 (1989)).

To obtain sufficient amounts of fucosyltransferase for large-scale reaction, the gene or cDNA that codes for the enzyme can be cloned and expressed as a recombinant soluble enzyme by someone with ordinary skill in the art. As a preferred method RNA can be extracted from the wild type CHO cells and LEC11 cells as described by Chirgwin et al.,

*Biochemistry* 18:5214–5299 (1979), and the poly A+ RNA isolated by chromatography on oligo(dT)-cellulose. Next, cDNA from the LEC-11 cells can be prepared as described by Sambrook et al., *Molecular Cloning: A Laboratory Manual*, 2nd Ed. (1989), Cold Spring Harbor Press, New York, which is incorporated herein by reference. The cDNAs that are common to both LEC11 and CHO cells can be subtracted using the method of Davis (*Handbook of Experimental Immunology*, Vol. 2, pp. 1–13 (1986)) using excess poly A+ RNA from wild type CHO cells, which do not express the desired fucosyltransferase, but otherwise have most of the mRNA species of LEC11 cells. A cDNA library can then be constructed in the CDM8 expression vector using the cDNA that was not subtracted (Seed, *Nature* 329:840–842 (1987)). Clones expressing the fucosyltransferase can be isolated using the expression cloning method described by Larsen et al., *Proc. Natl. Acad. Sci.* 86:8227–8231 (1989), employing transfection of COS-1 cells and screening for cells expressing the SLe$^x$ antigen with the CSLEX antibody or other antibody that is specific for the SLe$^x$ antigen. The full-length clone of the fucosyltransferase can then be used to produce a soluble recombinant enzyme as taught by Colley et al., supra.

Another source of SLe$^x$ is the plasma protein $\alpha_1$-acid glycoprotein, the carbohydrate moieties of which can be fucosylated to produce SLe$^x$ (see, *Alpha-Acid glycoprotein: Genetics, Biochemistry, Physiological Functions, and Pharmacology*, Bauman et al. ed. (Wiley 1989), and Walz, et al. *Science* 250:1132–1135 (1990), both of which are incorporated herein by reference).

Although enzymatic or combined chemical and enzymatic synthesis of SLe$^x$ compounds are preferred, chemical synthesis is also possible, as shown in Schemes II and IIa below.

Scheme II

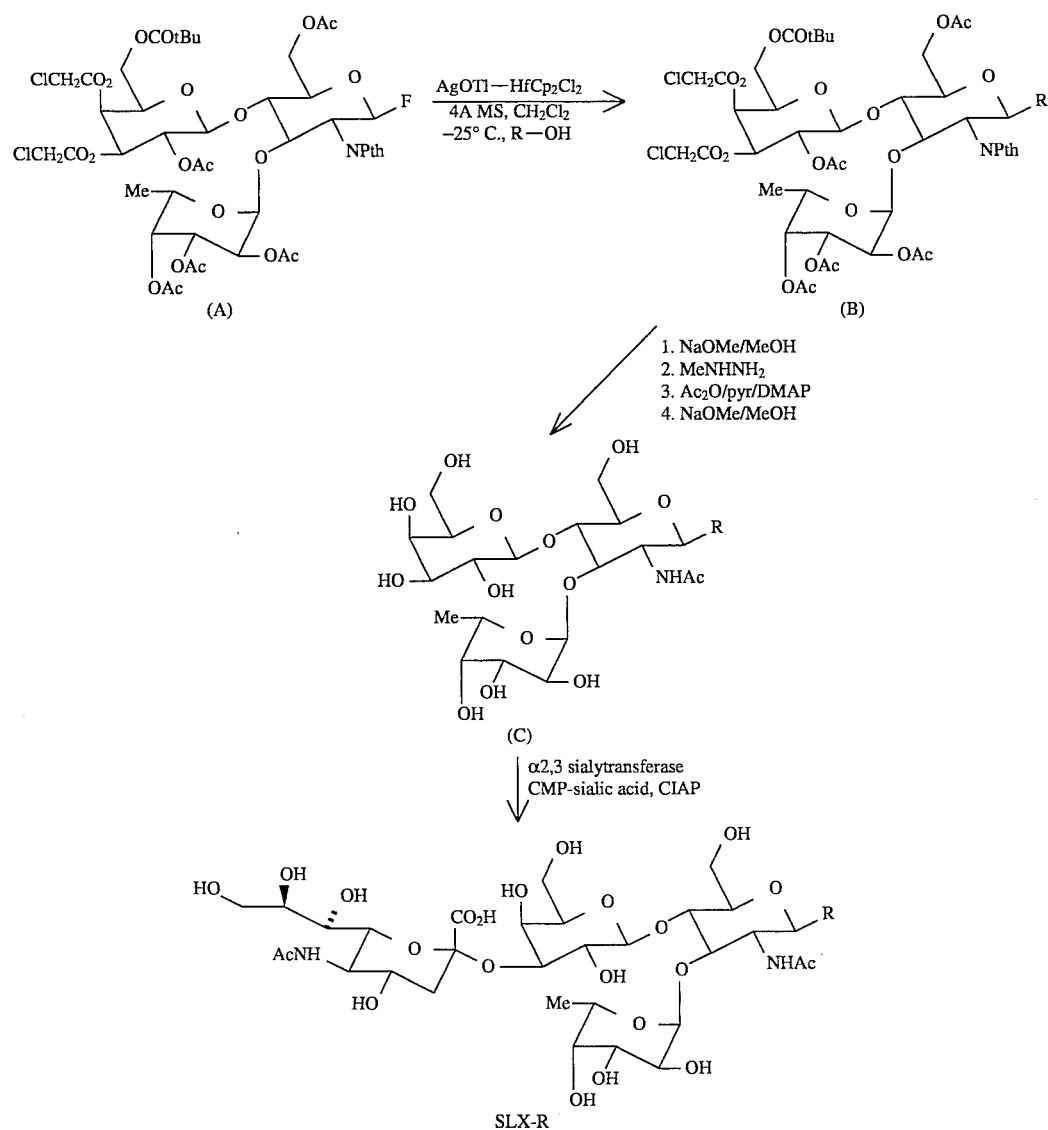

Scheme IIa

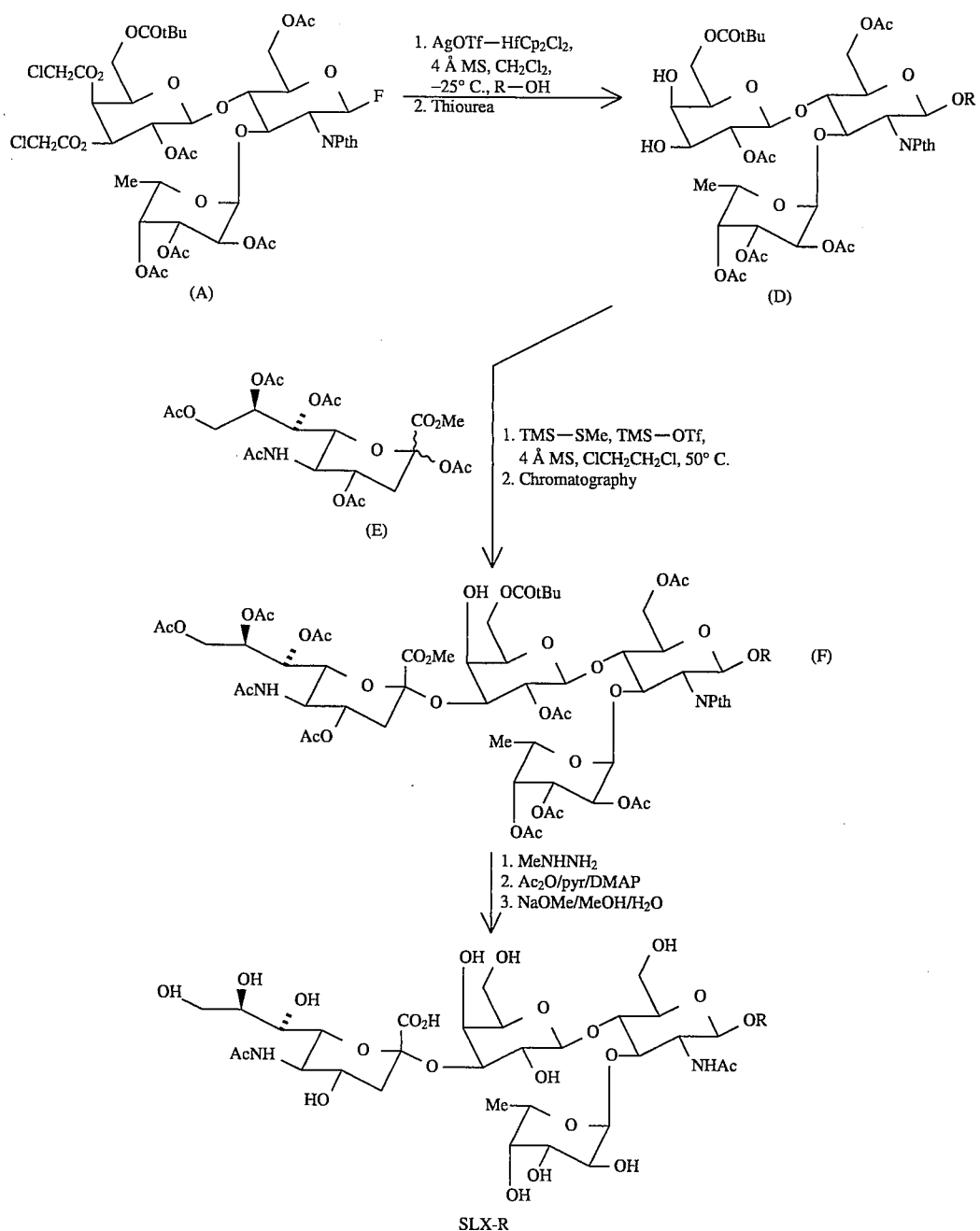

Component pieces of the SLe$^x$ structure have been synthesized. For instance, the preparation of sialic acid-containing glycosides, including SLe$^x$, is disclosed in European Patent Application No. 88311312.8, which is incorporated herein by reference. Nicolaou, et al., (*J. Amer. Chem. Soc.* 112:3693 (1990)) have published the total synthesis of the tumor-associated Lex family of glycosphingolipids. Therein is described the synthesis of the protected trisaccharide Galβ1,4(Fucα1,3)GlcNAc (A) as illustrated in Scheme II. Reaction of this intermediate with an appropriate glycosyl acceptor (e.g., an alcohol moiety) results in compound (B). Selective deprotection and acetylation of the glucosamine moiety are carried out essentially as described in Nicolaou, et al. to afford compound (C). Reaction of (C) with a sialyltransferase as described above furnishes the desired product SLe$^x$-R, although this may be produced in relatively low yield using Scheme II.

Modified fucosides may be included in the synthetic schemes to provide for SLe$^x$ analogues which vary in this moiety. For example, α-D-arabinosyl glycosides may be synthesized following known procedures, Nicolaou et al., *J. Amer. Chem. Soc.* 112:3693–3695 (1990) through the use of tri-O-benzyl arabinosyl halides. Other C-5 aryl or alkyl substituted arabinosyl moieties may be synthesized (Danishefsky et at., *J. Amer. Chem. Soc.* 107:1274 (1985), Danishefsky, *Aldrichimica Acta.* 19:59–68 (1986) and references therein), and introduced into the disaccharide in the same manner. All of these references are incorporated herein by reference.

According to alternative Scheme IIa, the trisaccharide (A) is partially deprotected to furnish (D), which is subsequently reacted with the peracetylated sialic acid methyl ester (E) following a procedure described by Kameyama et al., *XV Intl. Carbohyd. Sym.*, Abst. No. A096, (1990), and *Carbohydrate Res.*, 209:c1–c4 (1991) (which are incorporated herein by reference), yielding (F) after chromatographic purification. Treatment of (F) with with methylhydrazine, followed by N-acetylation, O-deacetylation and ester hydrolysis, furnishes $SLe^x$-R.

Preferred examples of R for scheme II and IIa include alkyl (straight chain, branched, saturated, mono- and poly-unsaturated); serine (D or L); serine containing peptides; di- and tri-alkanolamines (e.g. $[HO(CH_2)_n]_2NH$, $[HO(CH_2)_n]_3N$; wherein n=2 to 20, and the carbon chain is a straight chain, or is branched, unsaturated, or mono- or poly-unsaturated). R can also be aryl, substituted aryl (e.g., Me, OH, I; alone or in combination including $^{125}I$), alkylaryl, arylalkyl or other moiety, as the skilled artisan would include for the desired use. The introduction of iodine into phenolic compounds such as tyrosine is known in the art. Radical groups containing phenols are useful for the introduction of $^{125}I$ radioisotope, yielding compounds that are useful in diagnosis.

Since a ligand specific for selectin receptors has now been identified, isolated ligand molecules can also be used in the assays. The terms "isolated selectin-binding agent" or "isolated $SLe^x$ moiety" as used herein refer to a selectin binding compound that is in other than its native state, e.g., is not associated with the cell membrane of a cell that normally expresses the ligand. Thus, an isolated $SLe^x$ moiety may be a component of an isolated molecule, such as an oligosaccharide or a glycoconjugate. The isolated molecule may be synthesized or prepared from the membranes of $SLe^x$-bearing cells. Alternatively, the isolated selectin-binding agent or $SLe^x$ moiety may be associated with a liposome or attached to a solid surface before use in the assay. Methods for preparing selectin-binding liposomes and for immobilizing various biomolecules are extensively discussed below.

The pharmaceutical compositions of the present invention can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Example of specific defense system reactions include antibody response to antigens such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection (e.g., pulmonary infiltrates in bacterial pneumonias and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

By way of example, reperfusion injury is particularly amenable to treatment by compositions of the present invention. Compositions that inhibit a P-Selectin selectin-ligand interaction may be particularly useful for treating or preventing reperfusion injury. The present invention may be used prophylactically prior to heart surgery to enhance post-surgical recovery.

Because P-Selectin is stored in Weibel-Palade bodies of platelets and endothelial cells and is released upon activation by thrombin to mediate adhesion of neutrophils and monocytes, inhibitors of the P-Selectin -ligand interaction may be especially useful in minimizing tissue damage that often accompanies thrombotic disorders. For instance, such inhibitors may be of therapeutic value in patients who have recently experienced stroke, myocardial infarctions, deep vein thrombosis, pulmonary embolism, etc. The compounds are especially useful in pre-thrombolytic therapy.

Compositions of the invention find particular use in treating the secondary effects of septic shock or disseminated intravascular coagulation (DIC). Leukocyte emigration into tissues during septic shock or DIC often results in pathological tissue destruction. Furthermore, these patients may have widespread microcirculatory thrombi and diffuse inflammation. The therapeutic compositions provided herein inhibit leukocyte emigration at these sites and mitigate tissue damage.

The inhibitors of selectin-ligand interaction also are useful in treating traumatic shock and acute tissue injury associated therewith. Because the selectins play a role in recruitment of leukocytes to the sites of injury, particularly E-Selectin in cases of acute injury and inflammation, inhibitors thereof may be administered locally or systemically to control tissue damage associated with such injuries. Moreover, because such inhibitors are specific for sites of inflammation, e.g., sites where E-Selectin receptors are expressed, these compositions will be more effective and less likely to cause complications when compared to traditional anti-inflammatory agents.

Thus, the present invention also provides pharmaceutical compositions that can be used in treating the aforementioned conditions. The pharmaceutical compositions are comprised of biomolecules or other compounds which comprise an $SLe^x$ unit, antibodies which bind to $SLe^x$, or other compounds which inhibit the interaction between the $SLe^x$ ligand and selectin receptors, together with pharmaceutically effective carriers. A biomolecule of the present invention may be a peptide, polypeptide, protein (e.g., an immunoglobulin), carbohydrate (e.g., oligosaccharide or polysaccharide), glycoconjugate (e.g., glycolipid or glycoprotein), nucleic acid, and the like. The pharmaceutical compositions are suitable for use in a variety of drug delivery systems. For a brief review of present methods for drug delivery, see, Langer, *Science* 249:1527–1533 (1990), which is incorporated herein by reference.

In light of the complexity of the inflammatory response in mammals, one of skill will readily recognize that the pharmaceutical compositions of the present invention may comprise $SLe^x$ bearing compounds in admixture with other compounds known to interfere with the function of cellular adhesion molecules. For instance, members of the integrin family of adhesion molecules are thought to play a role in the extravasation of leukocytes at points of infection. For a review of intercellular adhesion receptors, including selectin receptors, and their role immune function, see Springer, *Nature* 346:425–434 (1990), which is incorporated herein by reference. In addition, successful treatment using the pharmaceutical compositions of the present invention may also be determined by the state of development of the condition to be treated. Since different adhesion molecules may be up or down regulated in response to a variety of factors during the course of the disease or condition, one of skill will recognize that different pharmaceutical compositions may be required for treatment of different inflammatory states.

In one embodiment, the SLe$^x$ ligand of the pharmaceutical composition can be used to target conventional anti-inflammatory drugs or other agents to specific sites of tissue injury. By using a selectin-binding moiety such as an SLe$^x$ ligand or SLe$^x$ mimetic to target a drug to a selectin receptor on, e.g., a vascular endothelial cell, such drugs can achieve higher concentrations at sites of injury. Side effects from the conventional antiinflammatory chemotherapeutic agents can be substantially alleviated by the lower dosages, the localization of the agent at the injury sites and/or the encapsulation of the agent prior to delivery.

The targeting component, i.e., the SLe$^x$ ligand or an SLe$^x$ mimetic which binds to a desired selectin, can be directly or indirectly coupled to the chemotherapeutic agent. The coupling, which may be performed by means generally known in the art, should not substantially inhibit the ability of the ligand to bind the receptor nor should it substantially reduce the activity of the chemotherapeutic agent. A variety of chemotherapeutics can be coupled for targeting. For example, anti-inflammatory agents which may be coupled include SLe$^x$-bearing compounds of the present invention, immunomodulators, platelet activating factor (PAF) antagonists, cyclooxygenase inhibitors, lipoxygenase inhibitors, and leukotriene antagonists. Some preferred moieties include cyclosporin A, indomethacin, naproxen, FK-506, mycophenolic acid, etc. Similarly, anti-oxidants, e.g., superoxide dismutase, are useful in treating reperfusion injury when targeted by a SLe$^x$ ligand or mimetic. Likewise, anticancer agents can be targeted by coupling the SLe$^x$ ligand or mimetic to the chemotherapeutic agent. Examples of agents which may be coupled include daunomycin, doxorubicin, vinblastine, bleomycin, etc.

The selectin receptor targeting may also be accomplished via amphipaths, or dual character molecules (polar:nonpolar) which exist as aggregates in aqueous solution. Amphipaths include nonpolar lipids, polar lipids, mono- and diglycerides, sulfatides, lysolecithin, phospholipids, saponin, bile acids and salts. These molecules can exist as emulsions and foams, micelles, insoluble monolayers, liquid crystals, phospholipid dispersions and lamellar layers. These are generically referred to herein as liposomes. In these preparations the drug to be delivered is incorporated as part of a liposome in conjunction with a SLe$^x$ ligand or mimetic which binds to the selectin receptor. Thus, liposomes filled with a desired chemotherapeutic agent can be directed to a site of tissue injury by the selectin-SLe$^x$ ligand interaction. When the liposomes are brought into proximity of the affected cells, they deliver the selected therapeutic compositions.

The liposomes of the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Methods used in sizing and filter-sterilizing liposomes are discussed below. The acyl chain composition of phospholipid may also affect the stability of liposomes in the blood. One preferred phosphatidylcholine is partially hydrogenated egg phosphatidylcholine.

Targeting of liposomes using a variety of targeting agents (e.g., ligands, receptors and monoclonal antibodies) is well known in the art. (see, e.g., U.S. Pat. Nos. 4,957,773 and 4,603,044, both of which are incorporated herein by reference). Glycoproteins and glycolipids of a variety of molecular weights can be used as targeting agents. Typically, glycoproteins having a molecular weight less than about 300,000 daltons, preferably between about 40,000 and about 250,000 are used, more preferably between about 75,000 and about 150,000. Glycolipids of molecular weight of less than about 10,000 daltons, preferably between about 600 and about 4,000, are used.

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., *J. Biol. Chem.*, 265:16337–16342 (1990) and Leonetti et al., *Proc. Natl. Acad. Sci.* (USA) 87:2448–2451 (1990), both of which are incorporated herein by reference).

Targeting mechanisms generally require that the targeting agents be positioned on the surface of the liposome in such a manner that the target agents are available for interaction with the selectin receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

Liposome charge is an important determinant in liposome clearance from the blood, with negatively charged liposomes being taken up more rapidly by the reticuloendothelial system (Juliano, *Biochem. Biophys. Res. Commun.* 63:651 (1975))and thus having shorter half-lives in the bloodstream. Liposomes with prolonged circulation half-lives are typically desirable for therapeutic and diagnostic uses. Liposomes which can be maintained from 8, 12, or up to 24 hours in the bloodstream provide sustained release of the selectin-ligand inhibitors of the invention, or may facilitate targeting of the inhibitors (which may be labelled to provide for in vivo diagnostic imaging) to a desired site before being removed by the reticuloendothelial system.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serves to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4,837,028, incorporated herein by reference.

Additionally, the liposome suspension may include lipid-protective agents which protect lipids and drug components against free-radical and lipid-peroxidative damages on storage. Lipophilic free-radical quenchers, such as alphatocopherol and water-soluble iron-specific chelators, such as ferrioxianine, are preferred.

A variety of methods are available for preparing liposomes, as described in, e.g., Szoka et at., *Ann. Rev. Biophys. Bioeng.* 9:467 (1980), U.S. Pat. Nos. 4,235,871, 4,501,728 and 4,837,028, incorporated herein by reference. One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration which is desired in the interior volume of the liposomes in the final liposome suspension. Typically the drug solution contains between 10–100 mg/ml in a buffered saline. The concentration of the targeting SLe$^x$ molecule or mimetic which binds a selectin is generally between about 0.1–20 mg/ml.

Following liposome preparation, the liposomes may be sized to achieve a desired size range and a relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more drug and targeting agent in free (non-encapsulated) form. Therefore, to maximize the advantages of liposomal targeted drug, it is important to remove free drug and targeting agent from the final injectable suspension.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a drug-free replacement medium. Alternatively, gel filtration can be used to separate large liposome particles from solute molecules.

Following treatment to remove free drug and/or targeting agent, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposome-ligand preparation may be administered parenterally or locally in a dose which varies according to, e.g., the manner of administration, the drug being delivered, the particular disease being treated, etc.

For pharmaceutical compositions which comprise the SLe$^x$ ligand, and/or SLe$^x$ mimetics which bind to selectin receptors, the dose of the compound will vary according to, e.g., the particular compound, the manner of administration, the particular disease being treated and its severity, the overall health and condition of the patient, and the judgment of the prescribing physician. For example, for the treatment of reperfusion injury, the dose is in the range of about 50 μg to 2,000 mg/day for a 70 kg patient. Ideally, therapeutic administration should begin as soon as possible after the myocardial infarction or other injury. The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

Preferably, the pharmaceutical compositions are administered intravenously. Thus, this invention provides compositions for intravenous administration which comprise a solution of the compound dissolved or suspended in a pharmaceutically acceptable carrier, preferably an aqueous carrier. A variety of aqueous carriers may be used, e.g., water, buffered water, 0.4% saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of $SLe^x$ ligand or mimetic, which may be combined with other $SLe^x$ ligands or mimetics to form a "cocktail" for increased efficacy in the pharmaceutical formulation, can vary widely, i.e., from less than about 0.05%, usually at or at least about 1% to as much as 10 to 30% by weight and will be selected primarily by fluid volumes, viscosities, etc., in accordance with the particular mode of administration selected. The cocktail may also comprise a monoclonal antibody which binds to selectin receptor, e.g., a monoclonal antibody to E-Selectin or P-Selectin, combined with the $SLe^x$ ligand, a ligand mimetic or a monoclonal antibody to the ligand, so as to effectively inhibit the ligand-receptor interaction. As described above, the cocktail components may be delivered via liposome preparations.

Thus, a typical pharmaceutical composition for intravenous infusion could be made up to contain 250 ml of sterile Ringer's solution, and 25 mg of the compound. Actual methods for preparing parenterally administrable compounds will be known or apparent to those skilled in the art and are described in more detail in for example, *Remington's Pharmaceutical Sciences*, 17th ed., Mack Publishing Company, Easton, Pa. (1985), which is incorporated herein by reference.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more $SLe^x$ ligands or mimetics of the invention, preferably about 20% (see, *Remington's*, supra).

For aerosol administration, the compounds are preferably supplied in finely divided form along with a surfactant and propellant. Typical percentages of $SLe^x$ oligosaccharide ligands or mimetics are 0.05% –30% by weight, preferably 1% –10%. The surfactant must, of course, be nontoxic, and preferably be soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1% –20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient, but generally range from about 0.5 mg to about 2,000 mg of $SLe^x$ oligosaccharide or $SLe^x$ mimetic per day for a 70 kg patient, with dosages of from about 5 mg to about 200 mg of the compounds per day being more commonly used.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of $SLe^x$ oligosaccharide or $SLe^x$ mimetic of this invention sufficient to effectively treat the patient.

The compounds may also find use as diagnostic reagents. For example, labeled compounds can be used to locate areas of inflammation or tumor metastasis in a patient suspected of having an inflammation. For this use, the compounds can be labeled with, for example, $^{125}I$, $^{14}C$, or tritium.

The following examples are offered by way of illustration, not by way of limitation.

EXAMPLE 1

Preparation of Pentasaccharide Z

This example describes the synthesis of a preferred pentasaccharide, Z. The structure of the intermediate compounds and the final product are shown in FIG. 12A. Each intermediate compound is identified by Roman numerals I through X.

Preparation of Ethyl β-D-galactopyranoside (I)

A solution of 2,3,4,6-tetra-O-acetyl-galactosyl bromide (2.5 kg) in dichloromethane (4 L) was added at a rate of 20–25 mL/min to a reactor charged with silver carbonate (3.13 kg, 11.4 mol), 4A molecular sieves (2.37 kg), dichloromethane (16 L), and anhydrous ethanol (4.0 L). Agitation was maintained to provide vigorous mixing of the reagents. Two hours after complete addition of the bromide solution, TLC on silica gel developed with hexane:ethyl acetate (1:1) showed no bromide present. At that time the reaction mixture was filtered through a celite pad (1 kg), and the filtrate was evaporated at 30°–35° C. under vacuum to give a brown oil (1.95 kg). This oil was dried under vacuum for 17 hours. $^1$H NMR (CDCL$_3$) δ: 5.36 (1H, d, J$_{3,4}$=3.7 Hz, H-4), 5.17 (1H, dd, J$_{2,3}$=11.0 Hz, H-2), 4.99 (1H, dd,H-3), 4.46 (1H, d, J$_{1,2}$=8.3 Hz, H-1), 2.15, 2.05, 2.04, 1.95 (12H, 4s, OAc), 1.21(3H, t, OCH$_2$CH$_3$).

The crude ethyl tetraacetyl galactopyranoside (1.95 kg) was dissolved in anhydrous methanol (11.7 L) and a 25% sodium methoxide in methanol solution (90 mL) was added dropwise. The solution was stirred for one hour at which time TLC on silica gel developed with ethyl acetate:methanol (2:1) showed no starting material to be present. The product had an R$_f$=0.6. The solution was neutralized by the addition of Amberlite IR-120(H$^+$) resin (0.6 kg) with stirring. When the solution pH was between pH 6 and pH 7, the resin was removed by filtration and the filtrate was evaporated under vacuum to afford a pale yellow solid. This solid was dissolved in boiling ethanol (11 L). The resulting solution was allowed to cool to 25° C. and then cooled to 0° C. to give a white precipitate. Filtration of this solid gave ethyl β-D-galactopyranoside (0.851 kg). $^1$H NMR (D$_2$O) δ: 4.38 (1H, d, J$_{1,2}$=8.0 Hz, H-1), 3.89 (1H, bd, J$_{3,4}$=3.7 Hz, H-4), 1.2 (3H, t, OCH$_2$CH$_3$).

Preparation of Ethyl
4,6-O-benzylidene-β-D-galactopyranoside (II)

Ethyl β-D-galactopyranoside (I) (0.851 kg, 4.09 mol) was charged into a 20 L rotovap flask with toluene sulfonic acid (1.5 g, 7.9 mmol). The evaporator flask was fixed to the evaporator, benzaldehyde dimethyl acetal (1.23 L, 8.18 mol) was added by aspiration and the mixture was tumbled for 4 hours. Between thirty and forty minutes after addition of the acetal, near complete solution was obtained followed rapidly by the appearance of a heavy precipitate. Rotation was continued for 4 hours at which time triethylamine (1.5 mL) was added to neutralize the reaction mixture. A vacuum was applied and the solvent was removed to give a solid mass. Hexane (6 L) was charged into the flask and the mixture tumbled for 0.5 hours. The resulting solid was filtered and washed on the filter with hexane:ethyl ether (1:1, 2 L). The white solid so obtained was dried under vacuum for 17 hours to give pure ethyl 4,6-O-benzylidene-β-D-galactopyranoside (1.0 kg, 3.38 mol) in 83% yield. $^1$H NMR (CDCl$_3$) δ: 7.53 (2H, m, aromatics), 7.37 (3H, m, aromatics), 5.57 (1H, s, CHPh), 4.29 (1H, d, J$_{1,2}$=7.0 Hz, H-1), 4.21 (1H, d, J$_{3,4}$=3.27 Hz, H-4), 1.29 (3H, t, OCH$_2$CH$_3$).

Preparation of Ethyl
2-O-benzoyl-4,6-O-benzylidene-β-D-galactopyranoside (III)

Ethyl 4,6-O-benzylidene-β-D-galactopyranoside (II)(0.924 kg, 3.12 mol) was put into a 20 liter reactor equipped with an air drive, a pressure equalizing addition funnel with gas inlet, cooling bath, and a gas outlet. Before sealing the flask, dichloromethane (9.3 L) and pyridine (2 L) were added which gave a homogeneous solution. The addition funnel was charged with chloroacetyl chloride (0.388 kg, 3.43 mol, 273 mL) as a 60% solution in dichloromethane. The flask was sealed and a low flow of dry nitrogen was begun. The bath was cooled to −65°±5° C. and the reaction mixture was stirred for 30 minutes. At that time dropwise addition of the acyl chloride solution was begun at a rate of 3–4 mL per minute. After complete addition of this solution the reaction mixture was maintained at −65°±5° C. for an additional 1 hour. At that time benzoyl chloride (0.614 kg, 4.37 mol, 0.507 L) was added to the reaction mixture at a rate of 8–12 mL per minute. The reaction mixture was allowed to warm to room temperature and left for 17 hours. The reaction mixture was filtered to remove precipitated salts and the filtrate was concentrated in vacuo to remove most of the dichloromethane. A small sample was set aside for NMR. $^1$H NMR (CDCl$_3$) δ: 5.75 (1H, dd, J$_{2,3}$=10.6 Hz, H-2), 5.56 (1H, s, CHPh), 5.25 (1H, dd, J$_{3,4}$=3.44 Hz, H-3), 4.69 (1H, d, J$_{1,2}$=8.48 Hz, H-1), 4.48 (1H, bd, H-4), 1.15 (3H, t, OCH$_2$CH$_3$). Water (180 mL) was added to the concentrate and the resulting mixture was agitated for two hours at 40° C. At that time the reaction mixture was further concentrated to give a yellow residue that was dissolved in dichloromethane (11 L) and transferred to a 50 liter extractor. The organic solution was successively extracted with ice cold aqueous 0.5N HCl (11 L), aqueous saturated sodium hydrogen carbonate (11 L), cold water (11 L), and the organic layer was dried over anhydrous sodium sulfate (1.0 kg), filtered, and the filtrate evaporated to give a yellow solid which was dried under high vacuum. This reaction was monitored by TLC on silica gel developed with hexane:ethyl acetate (1:1). This solid was dissolved in hot ethanol (9.5 L) which after cooling and filtration gave ethyl 2-O-benzoyl-4,6-O-benzylidene-β-D-galactopyranoside (0.737 kg, 1.85 mol)in 59% yield. $^1$H NMR (CDCl$_3$)δ: 5.59 (1H, s, CHPh), 5.36 (1H, dd, J$_{2,3}$=10.07 Hz, H-2), 4.64 (1H, d, J$_{1,2}$=8.21 Hz, H-1), 1.15 (3H, t, OCH$_2$CH$_3$).

To confirm that the benzoate is at the C-2 and that C-3 carries a free hydroxyl group, a drop of trichloroacetyl isocyanate was added to the NMR sample and the spectrum was reacquired. This spectrum contained a low field doublet of doublets at δ=5.27 typical of H-3 of galactose which is esterified at C-3. The original filtrate obtained from the reaction mixture contains additional quantities of product.

Preparation of Ethyl
2-O-benzoyl-4,6-O-benzylidene-3-O-
(3,4,6-tri-O-acetyl-2-deoxy-2-phthalimido-β-
D-glucopyranosyl)-β-D-galactopyranoside (IV)

Ethyl 2-O-benzoyl-4,6-O-benzylidene-β-D-galactopyranoside (III)(1.001 kg, 2.5 mol) was placed in a 20 L reactor that was equipped with a cooling bath, pressure equalizing addition funnel with gas inlet, agitator, and gas outlet. 4A Molecular sieves (1.03 kg), dichloromethane (6.6 L), collidine (0.367 L, 2.77 mol), and, after 15 min stirring, finally silver trifluoromethanesulfonate (0.689 kg, 2.641 mol) were added to the flask under a nitrogen flow. The addition funnel was charged with a solution of 3,4,6-tri-O-acetyl-2-deoxy-2-phthalimido-β-D-glucopyranosyl bromide (1.310 kg, 2.641 mol) dissolved in dichloromethane (2.40 L). The system was sealed and a low purge of nitrogen was maintained and agitation begun, first at room temperature for 1 hr, then cooling (−25° C.) of the reaction vessel was begun and the mixture was stirred at low temperature for another hour. The bromide solution was then added over 1–2 hours. The resulting mixture was allowed to come to ambient temperature and, after 17 hours, the mixture was filtered through a celite pad and the filtrate was washed with aqueous sodium thiosulfate (2M, 3.0 L), water (3 L), hydrochloric acid (1M, 2×2 L), sodium hydrogen carbonate (1M, 3.0 L), and finally water (3 L). The organic layer was dried over anhydrous sodium sulfate, filtered, and evaporated to give a solid. The solid was dissolved in isopropanol:ethyl acetate (1:1, 32 L) at reflux. On cooling to room temperature overnight, a first crop of ethyl 2-O-benzoyl-4,6-O-benzylidene-3-O-(3,4,6-tri-O-acetyl-2-deoxy-2-phthalimido-β-D-glucopyranosyl)-β-D-galactopyranoside was obtained, after filtration and drying. Concentration of the mother liquor (18 L evaporated) and leaving the resulting solution at room temperature overnight gave a second crop of material with acceptable purity. After TLC analysis, the two crops were pooled (1.479 kg, 1.816 mol, 72%). $^1$H NMR (CDCl$_3$) δ: 7.75 (14H, m, aromatics), 5.57 (1H, s, CHPh), 5.38 (1H, dd, J=7.89 Hz, J=10.5Hz), 5.16 (1H, t, J=9.99 Hz), 4.52 (1H, d, $J_{1,2}$=7.89, H-1), 2.08, 2.01, 1.88 (3H, 3s, OAc), 0.95 (3H, t, OCH$_2$CH$_3$).

Preparation of Ethyl
3-O-(2-N-allyloxycarbonyl-2-amino-2-deoxy-β-
D-glucopyranosyl)-β-D-galactopyranoside (V)

To ethyl 2-O-benzoyl-4,6-O-benzylidene-3-O-(3,4,6-tri-O-acetyl-2-deoxy-2-phthalimindo-β-D-glucopyranosyl)-β-D-galactopyranoside (IV) (1.017 kg, 1.25 mol) was added 80% acetic acid (10 L). The resulting mixture was heated to 90° C. for 1.25 hours, after which TLC on silica gel developed with ethyl acetate showed the product with $R_f$=0.5–0.6 and complete consumption of the starting material. The solution was evaporated to dryness, and the residue was dissolved in 1:1 ethanol:acetone (6 L) at 70° C. Deionized water (9.0 L) was added to the resulting solution to precipitate the product. The product was filtered and washed with water:acetone 9:1 (6 L) and air dried for 16 hours then dried under vacuum over sodium hydroxide pellets. A second crop was isolated by adding deionized water (4.5 L) to the mother liquor. This material was dried as described above. The yield of the diol was 0.707 kg (81%). $^1$H NMR (CDCl$_3$) δ: 5.67 (1H, dd, $J_{3',4'}$=9.07 Hz, $J_{2',3'}$=11.23 Hz, H-3'), 5.57 (1H, d, $J_{1',2'}$=9.21 Hz, H-1'), 5.32 (1H, dd, $J_{2,3}$=10.08 Hz, H-2), 5.12 (1H, t, $J_{4',5'}$=9.07 Hz, H-4'), 4.46 (1H, d, $J_{1,2}$=8.64, H-1), 2.14, 2.03, 1.78 (9H, 3s, OAc), 0.98 (3H, t, OCH$_2$CH$_3$).

Ethyl 2-O-benzoyl-3-O-(3,4,6-tri-O-acetyl-2-deoxy-2-phthalimido-β-D-glucopyranosyl)-β-D-galactopyranoside (0.645 kg, 0.882 mol) was dissolved in ethanol (6.5 L) with heating to reflux and stirring. Upon obtaining a clear solution, hydrazine hydrate (0.4 L, 8.25 mol) was added and the mixture heated to reflux, with continued stirring. A precipitate began to appear and after 16 hrs reflux, the reaction was complete as judged by TLC on silica gel developed with ethyl acetate:acetic acid:methanol:water 12:3:3:2. The product had an $R_f$=0.15. The reaction mixture was cooled to ambient temperature, then acetone (5 L) was added, with stirring. Continued stirring gave a homogeneous suspension which was filtered to give crude ethyl 3-O-(2-amino-2-deoxy-β-D-glucopyranosyl)-β-D-galactopyranoside, as a white, amorphous powder (0.4 kg) after drying under high vacuum in the presence of phosphorous pentoxide. This crude material was added to a mixture of methanol (5.5 L) and water (0.3 L). Sodium hydrogen carbonate (0.90 kg, 10.7 mol) was added, and the mixture was stirred for 30 min. At that time allyl chloroformate (0.140 L, 1.32 mol) was added, with continued stirring at room temperature. After 1 hour TLC on silica gel developed with ethyl acetate:acetic acid:methanol:water, 12:3:3:2 showed the product with $R_f$=0.6 and the reaction to be complete. The mixture was filtered, and the solid was washed with methanol (0.5 L). The filtrate was evaporated to give a residue. The residue was taken up in water (3.0 L) and extracted with dichloromethane (4.0 L). The aqueous layer was separated and washed with dichloromethane (1.0 L) and concentrated to give a solid. The solid mass was stirred vigorously for 2 hours with acetone:ethyl acetate (1:2, 3 L). The suspension was filtered and the solid was washed with ethyl acetate.

Drying under high vacuum in the presence of phosphorous pentoxide for 17 hours gave an off-white powder (0.444 kg). $^1$H NMR (D$_2$O) δ: 5.93 (1H, m, OCH$_2$CH=CH$_2$), 5.35–5.17 (2H, m, OCH$_2$CH=CH$_2$), 4.67 (1H, d, $J_{1',2'}$=8.13 Hz, H-1'), 4.35 (1H, d, $J_{1,2}$=8.10 Hz, H-1), 4.09 (1H, d, $J_{3,4}$=3.0 Hz, H-4), 1.19 (3H, t, OCH$_2$CH$_3$).

Preparation of Ethyl
(β-D-Galactopyranosyl)-(1-4)-O-
(2-N-allyloxycarbonyl-2-deoxy-β-
D-glucopyranosyl)-(1-3)-O-β-
D-galactopyranoside (VI)

This step describes the synthesis of a trisaccharide with a N-phthalimidolactosyl halide which is a suitable acceptor for enzymatic sialylation.

To a mixture of ethyl 2-O-benzoyl-4,6-O-benzylidene-β-D-galactopyranoside (III) (0.76 g, 1.9 mmol), 4A molecular sieves (2 g), dichloromethane (10 mL), collidine (0.278 mL, 2.1 mmol), and silver trifluoromethanesulfonate (0.522 g, 2 mmol) cooled to −25° C. was added dropwise a solution of 4-O-(2,3,4,6-tetra-O-acetyl-β-D-galactopyranosyl)-3,6-di-O-acetyl-2-deoxy-2-phthalimido-β-D-glucopyranosyl chloride (1.484 g, 2 mmol) dissolved in dichloromethane (5 mL). The resulting mixture was stirred and warmed to ambient temperature after complete addition of the chloride. After 2 hours the mixture was diluted with dichloromethane and filtered. The filtrate was washed successively with aqueous sodium bisulfite, aqueous hydrochloric acid, aqueous sodium hydrogen carbonate, and finally water. The organic layer was dried over anhydrous sodium sulfate, filtered and evaporated to give a solid mass that was recrystallized from dichloromethane:hexane. The fully blocked trisaccharide (0.66 g) was treated with 80% acetic acid (5 mL) at 80° C. for 2 hours at which time the solvent was removed by evaporation. The residue was coevaporated with toluene-ethyl acetate two times to give a residue which was dissolved in ethanol (10 mL). Hydrazine hydrate (0.3 mL) was added and the resulting mixture was refluxed for 17 hours to give a precipitate which was filtered to give a solid (0.45 g) after drying. This solid was dissolved in methanol:water 5:1 and treated with diallylpyrocarbonate (0.166 mL) for 1 hour. The resulting mixture was evaporated and partitioned between dichloromethane and water. The aqueous layer was separated and concentrated to give a residue which solidified upon trituration with ethyl acetate:acetone (4:2).

This provided the title trisaccharide (VI) which was enzymatically sialylated to give ethyl (sodium (5-acetamido-3,5-dideoxy-α-D-glycero-D-galactononulopyranosylonate))-(2-3)-O-(β-D-galactopyranosyl)-(1-4)-O-(2-N-allyloxycarbonyl-2-deoxy-β-D-glucopyranosyl)-(1-3)-O-β-D-galactopyranoside (VII) which was identical to that produced in the following procedure.

Preparation of Ethyl (sodium
(5-acetamido-3,5-dideoxy-α-D-glycero-
D-galactononulopyranosylonate))-(2-3)-O-
(β-D-galactopyranosyl)-(1-4)-O-
(2-N-allyloxycarbonyl-2-deoxy-β-D-glucopyranosyl)-
(1-3)-O-β-D-galactopyranoside (VII)

The following describes the enzymatic conversion of a disaccharide (V) to produce the title compound (VII) using galactosyl transferase and sialyl transferase.

To water (12 L), N-(2-hydroxyethyl)piperazine-N'-(2-ethanesulfonic acid) (0.410 kg) was added and the pH of the resulting solution was adjusted to 7.5. Bovine serum albumin (17 g) was added and the mixture stirred until a complete solution was obtained. Ethyl 3-O-(2-N-allyloxycarbonyl-2-amino-2-deoxy-β-D-glucopyranosyl)-β-D-galactopyranoside (V) (0.3 kg), glucose-1-phosphate (0.271 kg), phosphoenolpyruvate (0.177 kg), potassium chloride (0.087 kg), sodium azide (8.4 g), and uridine-5'-diphosphate (8.76 g) were added and the resulting mixture stirred until all of the solids are dissolved. Aqueous solutions of manganese chloride (1M, 506 mL) and magnesium chloride (1M, 168 mL) were then added. Pyruvate kinase (42,000U), uridine-5'-diphosphate-glucose pyrophosphorylase (2000U), inorganic pyrophosphatase (8400U), uridine-5'-diphosphate-galactose epimerase (91,000U), and uridine-5'-diphosphate-galactosyl transferase (8850U) were then added. The final volume of the reaction mixture was adjusted to 17 L with water. After 48 hours a solution of aqueous magnesium chloride (1M, 340 mL) was added. The reaction was monitored by TLC on silica gel developed with isopropanol:1M ammonium acetate 4:1. After 8–9 days TLC indicated that the reaction had proceeded to >95% at which time the following solution was prepared. A solution of N-(2-hydroxyethyl)piperazine-N'-(2-ethanesulfonic acid) (0.528 kg) was prepared in water (15 L) and the pH of the resulting solution was adjusted to 7.5. Bovine serum albumin (22 g), sodium azide (11.5 g), sialic acid (0.242 kg), phosphoenolpyruvate (0.395 kg), cytidine-5'-monophosphate (25 g), adenosine-5'-triphosphate (4.7 g), manganese chloride (1M, 780 mL) were added. To this was added pyruvate kinase (207,000U), myokinase (125,000U), cytidine-5'-monophosphate-N-acetylneuraminic acid synthetase (3245U), inorganic pyrophosphatase (9400U), and α2,3 sialyltransferase (1640U). The volume of this mixture was adjusted to 22 L and this solution was added to the galactosyl transferase reaction. The reaction was monitored by TLC on silica gel developed with isopropanol:1M ammonium acetate (4:1). After 10–12 days TLC indicates that the reaction had proceeded to give >95% of the title compound.

Preparation of Ethyl (methyl
(5-acetamido-3,5-dideoxy-4,7,8,9-tetra-
O-acetyl-α-D-glycero-
D-galacto-nonulopyranosylonate))-(2-3)-
O-(2,4,6-tri-O-acetyl-β-D-galactopyranosyl)-(1-4)-
O-(3,6-di-O-acetyl-2-N-allyloxycarbonyl-2-deoxy-β-
D-glucopyranosyl)-(1-3)-O-2,4,6-tri-O-acetyl-β-
D-galactopyranoside (VIII)

An aqueous solution (40 L) of ethyl (sodium (5-acetamido-3,5-dideoxy-α-D-glycero -D-galacto-nonulopyranosylonate))-(2-3)-O-(β-D-galactopyranosyl)-(1-4)-O-(2-N-allyloxycarbonyl-2-deoxy-β-D-glucopyranosyl)-(1-3)-O-β-D-galactopyranoside (VII) produced from the sequential action of galactosyl and sialyl transferases in the presence of the appropriate cofactors on the disaccharide (V) (0.320 kg) was filtered through paper. The filtrate was evaporated to a thick syrup in a 50 L rotavapor. The syrup was coevaporated twice with pyridine (2×2 L), then kept under vacuum for 20 hours. The evaporation flask was charged with a solution of N,N-dimethylaminopyridine (20 g) in pyridine (12 L). The rotavapor bath was charged with ice-water mixture, and rotation was continued while acetic anhydride (6 L) was added during a period of 1 hour. Two hours after complete addition more acetic anhydride (2 L) was added and the resulting mixture was left for 20 hours rotating slowly at room temperature. To ensure complete acetylation, more acetic anhydride (1 L) was added and the mixture was rotated for an additional 24 hours. The reaction was checked by TLC (ethyl acetate:hexane:ethanol, 10:10:3). Upon complete reaction vacuum was applied and 14 L of distillate collected.

To the resulting residue, methanol (15 L) was added over a period of 1 hour and the mixture was rotated at room temperature for 20 hours. At this time TLC on silica gel (ethyl acetate:hexane:ethanol, 10:10:3 and dichloromethane:acetone 3:2) showed complete conversion of the lactone to a slower-moving spot which is the methyl ester mono hydroxy compound. The mixture was then concentrated (18 L evaporated) and the mixture was cooled in ice water while acetic anhydride (3 L) was added over a period of 30 minutes. The mixture was left for 20 hours. TLC on silica gel (dichloromethane:acetone 3:2) showed complete acetylation with the product running slightly higher. Methanol (1 L) was added to destroy excess acetic anhydride during which a slight exotherm was noticed. After 1 hour, the mixture was concentrated to a syrup, which was transferred to a 50 L extractor with the aid of ethyl acetate-water mixture (13/13 L). The mixture was agitated vigorously. After phase separation, the lower aqueous layer was drawn off, and the remaining organic layer was filtered through paper. The filtrate was washed with 5% aqueous hydrochloric acid (15 L, the aqueous layer should still be strongly acidic to pH-paper after washing), and aqueous 1M sodium bicarbonate (15 L, the aqueous layer should still be alkaline to pH paper after washing). The organic layer was then transferred to a 20 L container and dried over anhydrous sodium sulfate and filtered. The filtrate was concentrated to a semi-solid residue. This residue was dissolved in dichloromethane (3 L), and applied to a silica gel column (10 kg), packed in dichloromethane. Elution first with dichloromethane (25 L), then with 3:1 dichloromethane:acetone (25 L), and finally with 1:1 dichloromethane:acetone (50 L) gave fractions containing product. Base-line separation was achieved from the disaccharide material, but very little separation was achieved from the traces of slightly faster moving material. The fractions containing product were evaporated, and redissolved in dichloromethane (1.5 L). This solution was slowly added to a vigorously stirred mixture of ethyl ether (7.5 L) and hexane (10 L). The resulting precipitate was filtered and washed with 2:1 ether:hexane, air-dried overnight, then dried in high vacuum for 48 hours. The precipitate (0.61 kg) was shown to be the title compound by NMR. $^1$H NMR contained a small amount of residual solvent (1–5%, weight/weight). $^1$H NMR (CDCl$_3$) δ: 4.67 (d, 1H, H-1"), 4.49 (d, 1H, H-1'), 4.33 (d, 1H, H-1).

Preparation of Ethyl (methyl
(5-acetamido-3,5-dideoxy-4,7,8,9-tetra-
O-acetyl-α-D-glycero-D-galacto-
2-nonulopyanosylonate))-(2,3)-0-
(3,4,6-tri-0-acetyl-β-D-galactopyranosyl)-
(1,4)-0-(2-acetamido-2-deoxy-6-0-acetyl-β-
D-glucopyranosyl)-(1,3)-0-(2,4,6-tri-
O-acetyl-β-D-galactopyranoside) (IX)

To a solution of blocked tetrasaccharide (VIII) (0.532 kg, 0.37 mol) in dry tetrahydrofuran (8 L) was added polymethylhydrosiloxane (PMSH, 46 mL, 0.14 mol). Then Pd(PPH$_3$)$_4$(14 g, 1.17 mmol) was added and the mixture was degassed under vacuum. The resulting reaction mixture was then stirred at room temperature for 17 hours when TLC (10:10:3, ethyl acetate:hexane:ethanol) showed completion of the reaction. To the reaction mixture was added acetic acid (36 mL, 0.55 mol) and piperidine (60 mL, 0.65 mol). The mixture was stirred at room temperature overnight until TLC (95:5, dichloromethane:methanol) showed completion of the reaction. Evaporation of solvent in vacuo gave a residue which was dissolved in dichloromethane (4 L). This solution was washed successively with water (4 L), 2% aqueous hydrochloric acid (4 L), aqueous sodium hydrogen carbonate (4 L), and finally water (4 L). The organic layer was dried over anhydrous sodium sulfate, filtered and the filtrate evaporated to give a syrup. This syrup was dissolved in methanol (2 L), activated charcoal (200 g) was added and the resulting mixture was heated with stirring to 55° C. for 2 hours. After cooling the mixture was filtered and the filtrate was concentrated to give a residue. This residue was dissolved in dichloromethane (1 L) and added dropwise to a mixture of hexane:ether (1:1, 12 L) to give 0.46 kg of the title compound as a white solid. $^1$H NMR (CD$_3$OD): δ1.15 (t, 3H, J=7.0 Hz, —OCH$_2$CH$_3$); 1.50 (t, 1H, J=12.3 Hz, H-3a of NANA); 1.80, 1.91, 1.96, 2.01, 2.02, 2.04, 2.05, 2.07, 2.08, 2.09, 2.10, 2.16, 2.26 (13-Ac); 2.55 (dd, 1H, J=4.6, 12.3 Hz, H-3e of NANA); 3.84 (S, 3H, COOCH$_3$).

Preparation of Ethyl (methyl (5-acetamido-3,5-dideoxy-4,7,8,9-tetra-O-acetyl-α-D-glycero-D-galacto-2-nonulopyanosylonate))-(2-3)-O-(2,4,6-tri-O-acetyl-β-D-galactopyranosyl)-(1-4)-O-((2,3,4-tri-O-benzyl-α-L-fucopyranosyl)-(1-3))-O-(2-acetamido-6-O-acetyl-2-deoxy-β-D-glucopyranosyl)-(1-3)-O-2,4,6-tri-O-acetyl-β-D-galactopyranoside (X)

To a solution of the alcohol (IX) (0.118 kg, 0.090 mol) in a mixture of dichloromethane (250 mL) and dimethylformamide (60 mL) was added tetraethylammonium bromide (18.8 g, 0.090 mol). The mixture was then stirred with molecular sieves (4A, 0.250 kg) under nitrogen at room temperature for 6 hours. To the above mixture was added freshly prepared tri-O-benzyl-α-L-fucopyranosyl bromide (0.180 kg, 0.360 mol) in dichloromethane (100 mL). The reaction mixture was then stirred under nitrogen at room temperature for 36 hours until TLC (10:10:3, ethyl acetate:hexane:ethanol) showed completion of the reaction. The reaction mixture was treated with a mixture of methanol (30 mL) and diisopropylethylamine (30 mL) and was stirred at room temperature for 30 minutes. The mixture was diluted with 1 L of dichloromethane and filtered through a bed of celite. The filtrate was washed with aqueous saturated sodium bicarbonate (1.5 L) and water (2 L), and the organic layer dried over magnesium sulfate, filtered, and concentrated to a syrup. This syrup was chromatographed on silica gel (3.5 kg silica gel, 230–400 mesh, ethyl acetate:hexane:ethanol, 5:5:1) to give the title compound (0.110 kg, 73%) as an amorphous solid. $^1$H NMR (CDCl$_3$): δ1.17 (t, 3H, J=7.2 Hz, —OCH$_2$CH$_3$), 1.18 (d, 3H, J=7.0 Hz, CH$_3$ of Fuc), 1.60, 1.78, 1.84, 1.99, 2.01, 2.02, 2.04, 2.04, 2.06, 2.06, 2.07, 2.15, 2.19 (13-Ac), 2.55 (dd, 1H, J=4.4, 12.2 Hz, H-3e of NANA), 3.82 (s, 3H, COOCH$_3$), 7.4–7.6, (15H, aromatic).

Preparation of Ethyl (sodium (5-acetamido-3,5-dideoxy-α-D-glycero-D-galacto-2-nonulopyanosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside (Z)

To a solution of compound X (105 g, 61 mmol) in acetic acid (900 mL) was added palladium hydroxide on charcoal (20 g, 20% Pd). The reaction mixture was purged two times with hydrogen and then stirred under a hydrogen atmosphere for 8 hours until TLC (90:10, dichloromethane:methanol) showed completion of the reaction. The reaction vessel was purged several times with nitrogen and the reaction mixture was filtered through a bed of celite to remove the catalyst. The celite pad was washed with ethyl acetate several times. Concentration of the filtrate gave the debenzylated product as a white glass (about 97 g). The white glass was dried over high vacuum overnight and was dissolved in ethyl acetate (500 mL). The product triol (79 g, 89%) was precipitated out as white solid with addition of 1 L of a mixture of ether and hexane (8:2). A proton spectrum of the product showed the complete absence of aromatic protons.

To a solution of the triol (79 g, 50 mmol) in methanol (1 L) was added a solution of sodium methoxide (70 mL, 25% w/v). The reaction mixture was stirred at room temperature for 17 hours. Water (100 mL) was added and the mixture was stirred at room temperature for an additional 24 hours until TLC on silica gel (7:2:1, isopropanol:NH$_4$OH:H$_2$O) showed completion of the reaction. To the reaction mixture was added 150 mL of AG-50 H+ ion-exchange resin, which had been thoroughly washed with methanol, and the resulting mixture was stirred at room temperature for 30 minutes. The ion-exchange resin was removed by filtration and filtrate was concentrated to dryness to provide a white glass. The material was dissolved in methanol (300 mL) and filtered through a 0.22 μ nylon membrane. The filtrate was diluted with ethyl ether (300 mL) to give the free pentasaccharide (48 g, 84%) as a white solid. $^1$H NMR (D$_2$O): δ1.10 (d, 3H, J=6.5 Hz, CH$_3$ of Fuc); 1.16 (t, 3H, J=7.0 Hz, —OCH$_2$CH$_3$); 1.74 (t, 1H, J=12.2 Hz, H-3a of NANA); 1.95, 1.96 (2-Ac); 2.72 (dd, 1H, J=4.4, 12.2 Hz, H-3e of NANA); 4.32 (d, 1H, J=8.0 Hz, β-anomeric); 4.46 (d, 1H, J=7.4 Hz, β-anomeric); 4.65 (d, 1H, J=7.9 Hz, β-anomeric); 5.06 (d, 1H, J=4.1 Hz, α-anomeric of fucose).

Compounds XII-XXVI (FIG. 12B) can be synthesized using the general methodology described above, using techniques well known to one of skill in the art. FIG. 12B also provides comparisons of the blocking abilities of the compounds relative to Z. The assay described in Example 16 was used to measure blocking of E-selectin mediated binding. The concentration of oligosaccharide required to achieve 50% inhibition (IC$_{50}$) of control adhesion was used to compare analogs for potency.

In FIG. 12B, the synthesis of compounds XII–XX and XXII–XXVI utilized an enzymatic fucosidation step (Mollicone, R; Gibaud, A.; Francois, A.; Ratcliffe, M.; Oriol, R. *Eur. J. Biochem.* 191, 169–176 (1990)) to replace the steps reported previously for transforming VII to Z.

Compounds XII and XIII were synthesized beginning with the ethyl glycoside of the appropriately substituted pyranosides. Condensation of each of the ethyl pyranosides with 4-O-(2,3,4,6-tetra-O-acetyl-β-D-galactopyranosyl)-3-6-di-O-acetyl-2-deoxy-2-phthalimido-β-D-glucopyranosyl chloride provides the corresponding trisaccharides which were independently carried through the synthesis to the tetrasaccharide as described for compound VII, above. Enzymatic fucosidation of the tetrasaccharides then provided the pentasaccharides XII and XIII.

XII: Ethyl (ammonium (5-acetamido-3,5-dideoxy-α-D-glycero-D-galacto-2-nonulopyanosylonate))-(2-3)-O-(β-D-galactopyranosyl)-(1-4)-((α-L- fucopyranosyl)-(1- 3))-O-(2-acetamido-2-deoxy-β-D-glucopyranosyl)-(1-3)-O -β-L-arabinopyranoside.

$^1$H NMR (D$_2$O, 300 MHz) δ5.14 (d, J=3.8, Hz, 1H, H-1 Fuc), 4.55 (m, 2H, H-1 Glc, Gal), 4.34 (d, J=8.0 Hz, 1H, H-1

Arab), 4.17 (d, J=2.2 Hz, 1H, H-4 Gal), 4.06 (dd, J=3.0, 9.8 Hz, 1H, H-3 Gal), 4.03–3.52 (m, 25H), 2.78 (dd, J=12.4, 4.5 Hz, 1H, H-3(eq) NeuAc), 2.06 (s, 3H, NHAc), 2.04 (s, 3H, NHAc), 1.80 (dd, J=12.4, 12.4 Hz, 1H, H-3(ax) NeuAc), 1.28 (t, 3H, $CH_2CH_3$), 1.19 (d, J=6.4 Hz, 3H, H-6 Fuc).

XIII: 3(S)-O-(1(R)-O-ethyl-pyranosyl) (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside.

$^1$H NMR ($D_2O$, 300 MHz) δ5.13 (d, J=3.8, Hz, 1H, H-1 Fuc), 4.55 (m, 3H, H-1 Gal, Glc, Pyr), 4.11 (dd, J=2.9, 9.8 Hz, 1H, H-3 Gal) 4.05–3.42 (m, 26H), 2.80 (dd, J=12.4, 4.5 Hz, 1H, H-3(eq) NeuAc), 2.25 (bm, 1H, Pyr), 2.06 (s, 6H, NHAc), 2.15–1.97 (bm, 2H, Pyr), 1.82 (dd, J=12.4, 12.4 Hz, 1H, H-3(ax) NeuAc), 1.55 (bm, 1H, Pyr), 1.21 (m, 6H, $CH_2CH_3$ and H-6 Fuc).

The preparation of compounds XIV–XVI began by condensing the monoprotected cyclohexanediols with 3,4,6-tri-O-acetyl-2-deoxy-2-phthalimido-α-D-glucopyranosyl bromide as described for compound VI. The corresponding trisaccharides were converted to the tetrasaccharides using procedures similar to that described for compound VI, above. Enzymatic fucosidation of the tetrasaccharides then provided the corresponding pentasaccharides.

XIV: 1(R)-O-(2(R)-Cyclohexanediol (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside.

$^1$H NMR ($D_2O$, 300 MHz) δ5.10 (d, J=3.95, Hz, 1H, H-1 Fuc), 4.70 (d, J=7.4 Hz, 1H, H-1 Glc), 4.50 (d, J=7.8 Hz, 1H, H-1 Gal), 4.07 (dd, J=2.8, 9.8 Hz, 1H, H-3 Gal), 4.00–3.48 (m, 23H), 2.75 (dd, J=12.4, 4.4 Hz, 1H, H-3(eq) NeuAc), 2.02 (s, 6H, NHAc), 1.78 (dd, J=12.4, 12.4 Hz, 1H, H-3(ax) NeuAc), 1.78–1.50 (bm, 5H, cyclhex), 1.30 (bs, 3H, cychex), 1.15 (d, J=6.5 Hz, 3H, H-6 Fuc).

XV: 1(R)-O-(2(S)-Cyclohexanediol (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside.

$^1$H NMR ($D_2O$, 300 MHz) δ5.10 (d, J=3.95, Hz, 1H, H-1 Fuc), 4.59 (d, J=7.7 Hz, 1H, H-1 Glc), 4.50 (d, J=7.8 Hz, 1H, H-1 Gal), 4.08 (dd, J=2.9, 9.8 Hz, 1H, H-3 Gal), 3.98–3.42 (m, 23H), 2.76 (dd, J=12.4, 4.4 Hz, 1H, H-3(eq) NeuAc), 2.03 (s, 3H, NHAc), 2.02 (s, 3H, NHAc), 1.91 (bm, 2H, cychex), 1.79 (dd, J=12.4, 12.4 Hz, 1H, H-3(ax) NeuAc), 1.65 (bm, 2H, cychex), 1.26–1.11 (m, 4H, cychex), 1.16 (d, J=6.5 Hz, 3H, H-6 Fuc).

XVI: 1(S)-O-(2(R)-Cyclohexanediol (ammonium (5-acetamido-3,5-dideoxy-α-D-glycero-D-galacto-2-nonulopyranosylonate))-(2-3)-(β-D-galactopyranosyl)-(1-4)-((α-L-fucopyranosyl)-(1-3))-O-2-acetamido-2-deoxy-β-D-glucopyranoside.

$^1$H NMR ($D_2O$, 300 MHz) δ5.10 (d, J=3.95, Hz, 1H, H-1 Fuc), 4.57 (d, J=8.0 Hz, 1H, H-1 Glc), 4.50 (d, J=7.7 Hz, 1H, H-1 Gal), 4.07 (dd, J=2.8, 9.8 Hz, 1H, H-3 Gal), 4.00–3.48 (m, 23H), 2.75 (dd, J=12.4, 4.4 Hz, 1H, H-3(eq) NeuAc), 2.01 (s, 6H, NHAc), 1.78 (dd, J=12.4, 12.4 Hz, 1H, H-3(ax) NeuAc), 1.82–1.74 (bm, 1H, cyclhex), 1.57 (bs, 3H, cychex), 1.44–1.25 (bm, 4H, cyclhex), 1.15 (d, J=6.5 Hz, 3H, H-6 Fuc).

The synthesis of compound XVII began by condensing an appropriately substituted galactoside with 4-O-(2,3,4,6-tetra-O-acetyl-β-D-galactopyranosyl)-3,6-di-O-acetyl-2-deoxy-2-azido-α-D-glucopyranosyl imidate (Bommer, R.; Kinzy, W.; Schmidt, R.R. *Liebigs Ann. Chem.* 425–433 (1991)) to produce a trisaccharide using techniques well known to one of skill in the art. The trisaccharide was converted to the tetrasaccharide using enzymatic sialylation as described for compound VI. Enzymatic fucosidation of the tetrasaccharide then provided the pentasaccharide XVII.

XVII: 5-Methoxycarbonylpentyl (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-α-D-glucopyranosyl)-(1-3)-O-β-D-galactopyranoside.

$^1$H NMR ($D_2O$, 300 MHz) δ5.11 (d, J=3.8, Hz, 1H, H-1 Fuc), 4.72 (d, 1H, H-1 Glc), 4.51 (d, J=8.1 Hz, 1H, H-1 Gal), 4.37 (d, J=7.8 Hz, 1H, H-1 Gal), 4.12 (d, J =2.6 Hz, 1H, H-4 Gal), 4.08 (dd, J=3.3, 9.8 Hz, 1H, H-3 Gal), 4.00–3.47 (m, 28H), 3.69 (s, 3H, OMe), 2.77 (dd, J=12.4, 4.5 Hz, 1H, H-3(eq) NeuAc), 2.03 (s, 3H, NHAc), 2.02 (s, 3H, NHAc), 1.80 (dd, J=12.4, 12.4 Hz, 1H, H-3(ax) NeuAc), 1.62 (m, 4H, alkyl), 1.41 (m, 2H, alkyl), 1.17 (d, J=6.4 Hz, 3H, H-6 Fuc).

The synthesis of compound XX began by reacting the benzyl galactoside, prepared in a similar fashion to compound III in which the ethyl group is replaced by benzyl, with 3,4,6-tri-O-acetyl-2-deoxy-2-phthalimido-α-D-glucopyranosyl bromide, as described for compound IV, above. Conversion of this disaccharide to the tetrasaccharide was similar to that reported for compound VII and the pentasaccharide XX was prepared by enzymatic fucosidation.

XX: Benzyl (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside.

$^1$H NMR ($D_2O$, 300 MHz) δ7.43 (m, 5H, phenyl), 5.10 (d, J=3.8, Hz, 1H, H-1 Fuc), 4.67 (d, J=8.2 Hz, 1H, H-1 Glc), 4.50 (d, J=7.8 Hz, 1H, H-1 Gal), 4.42 (d, J=7.6 Hz, 1H, H-1 Gal), 4.12 (d, J=2.6 Hz, 1H, H-4 Gal), 4.06 (dd, J=3.5, 9.8 Hz, 1H, H-3 Gal), 4.00–3.47 (m, 26H), 2.74 (dd, J=12.4, 4.5 Hz, 1H, H-3(eq) NeuAc), 2.01 (s, 3H, NHAc), 1.98 (s, 3H, NHAc), 1.78 (dd, J=12.4, 12.4 Hz, 1H, H-3(ax) NeuAc), 1.14 (d, J=6.4 Hz, 3H, H-6 Fuc).

The preparation of compound XVIII utilized the disaccharide intermediate reported above for compound XX. The benzyl group of the disaccharide was removed by hydrogenation, a technique well-known to one of skill in the art, and the intermediate product was convened to the pentasaccharide as described for compound XX, above.

XVIII: (sodium (5-Acetamido-3,5-dideoxy-β-D-glycero-D-galacto-2-nonulopyranosylonate))-(2-3)-(β-D-galactopyranosyl)-(1-4)-((α-L-fucopyranosyl)-(1-3))-O-(2-acetamido-2-deoxy-β-D-glucopyranosyl-(1-3)-O-D-galactopyranoside.

$^1$H NMR ($D_2O$, 300 MHz) δ5.20 (d, J=3.3 Hz, H-1 Gal), 5.10 (d, J=3.7, Hz, H-1 Fuc), 4.54 (d, J=7.7 Hz, H-1), 4.51 (d, J=7.7 Hz, H-1), 4.19 (bd, H-4 Gal), 4.14 (d, J=2.9 Hz, H-4 Gal), 4.06 (dd, J=2.4, 9.8 Hz, H-3 Gal), 4.00–3.47 (m), 2.76 (dd, J=12.4, 4.5 Hz, H-3(eq) NeuAc), 2.01 (s, 6H, NHAc), 1.78 (dd, J=12.4, 12.4 Hz, H-3(ax) NeuAc), 1.15 (d, J=6.4 Hz, H-6 Fuc).

The synthesis of compound XIX condensed the 1,5-anhydro-galactoside prepared by a tin hydride reduction of 2,3,4,6-tetra-O-acetyl-α-D-galactopyranosyl bromide (Witczak, Z. J.; Whistler, R. L. *Carb. Res.* 150, 121–131 (1986)) with 1,3,4,6-tetra-O-acetyl-2-deoxy-2-acetamido-β-D-glucopyranoside (Aldrich) (Kiso, M.; Anderson, *L. Garb. Res.* 136, 309–323 (1985)) to provide the disaccharide. The disaccharide was converted to the tetrasaccharide in a similar manner to that described for compound VII. Enzymatic fucosidation afforded XIX.

XIX: (Ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl )-(1-3))-O-(2-acetamido-2-deoxy-β-D-glucopyranosyl)-(1-3)-O-β-D-1,5-anhydrogalactopyranoside.

$^1$H NMR (D$_2$O, 300 MHz) δ5.10 (d, J=3.95, Hz, 1H, H-1 Fuc), 4.73 (d, J=8.0 Hz, 1H, H-1 Glc), 4.52 (d, J=7.8 Hz, 1H, H-1 Gal) 4.15 (d, J=3.1 Hz, 1H, H-4 Gal), 4.08 (dd, J=3.0, 9.8 Hz, 1H, H-3 Gal), 4.00–3.49 (m, 27H), 3.19 (dd, J=11.2, 11.2 Hz, 1H, H-1 Gal), 2.76 (dr, J=12.4, 4.4 Hz, 1H, H-3(eq) NeuAc), 2.02 (s, 3H, NHAc), 2.01 (s, 3H, NHAc), 1.78 (dd, J=12.4, 12.4 Hz, 1H, H-3(ax) NeuAc), 1.15 (d, J=6.5 Hz, 3H, H-6 Fuc).

The synthesis of compound XXI began by removing the allyloxy carbonyl group of compound VIII as described for compound IX. Heating the amine in acetic acid in methanol at 50° C. then prepared the deacylated compound ethyl (methyl (5-acetamido-3,5-dideoxy-4,7,8,9-tetra-O-acetyl-α-D-glycero-D-galacto-2-nonulopyranosylonate) )-(2-3)-O-(3,4,6-tri-O-acetyl-β-D-galactopyranosyl)-(1-4)-O-(2-amino-6-O-acetyl-β-D-glucopyranosyl)-(1,3)-O-(2,4,6-tri-O-acetyl)-β-D-galactopyranoside. Acylation with allyloxy carbonyl chloride as described for compound V followed by chemical fucosidation, hydrogenation and deacetylation as described for compounds X and XI then provided compound XXI.

XXI: Ethyl (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-propylcarbamoyl-2-deoxy-β-D-glucopyranosyl)-(1-3)-O-β-D-galactopyranoside.

$^1$H NMR (D$_2$O, 300 MHz) δ5.15 (d, J=3.9 Hz, 1H, H-1 Fuc), 4.70 (d, J=8.5 Hz, 1H, H-1 Glc), 4.48 (d, J=7.8 Hz, 1H, H-1 Gal), 4.35 (d, J=7.8 Hz, 1H, H-1 Gal), 4.11 (d, J=3.0 Hz, 1H, H-4 Gal), 4.09–3.46 (m, 30H), 2.73 (dd, J=12.4, 4.5 Hz, 1H, H-3(eq) NeuAc), 2.00 (s, 3H, NHAc), 1.78 (dd, J=12.4, 12.4 Hz, 1H, H-3(ax) NeuAc), 1.19 (m, 2H, propyl), 1.21–1.12 (m, 6H, CH$_2$CH$_3$ and H-6 Fuc), 0.87 (t, 3H, CH$_3$ alkyl).

The synthesis of compound XXII utilized enzymatic sialylation as described for compound VII, and fucosidation of the 2-deoxy-1,5-anhydro-lactone.

XXII: (Ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-deoxy-1,5-anhydro-D-glucopyranoside.

$^1$H NMR (D$_2$O, 300 MHz) δ5.04 (d, J=3.8, Hz, 1H, H-1 Fuc), 4.53 (d, J=7.6 Hz, 1H, H-1 Gal), 4.11 (dd, J=3.1, 9.8 Hz, 1H, H-3 Gal), 4.06–3.44 (m, 22 H), 2.78 (dr, J =12.4, 4.5 Hz, 1H, H-3(eq) NeuAc), 2.20 (bm, 1H, H-2 Glc), 2.02 (s, 3H, NHAc), 1.83 (dr, J=12.2, 12.2 Hz, 1H, H-3(ax) NeuAc), 1.62 (bm, 1H, H-2 Glc), 1.21 (d, J =6.4 Hz, 3H, H-6 Fuc).

Compounds XXIII and XXIV were prepared by condensing either alkyl 2,4,6-tri-O-benzyl-β-D-galactoside, where alkyl is octyl or decyl, with 4-O-(2,3,4,6-tetra-O-acetyl-β-D-galactopyranosyl)-3,6-di-O-acetyl-2-deoxy-2-phthalimido-β-D-glucopyranosyl chloride to produce the trisaccharides in a similar manner as that described for compound VI, above. Enzymatic sialylation, as described for compound VII, and fucosidation then afforded the pentasaccharides XXIII and XXIV, respectively.

XXIII: Octyl (sodium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranosyl.

$^1$H NMR (D$_2$O/DOOCCD$_3$, 300 MHz) δ5.14 (bd, 1H, H-1 Fuc), 4.52 (d, J=7.8 Hz, 1H, H-1 Gal), 4.36 (d, J=7.7 Hz, 1H, H-1 Gal), 4.14 (bd, 1H, H-4 Gal), 4.08 (bdd, 1H, H-3 Gal), 4.11–3.49 (m, 29H), 2.77 (bdd, 1H, H-3(eq) NeuAc), 2.02 (6H, NHAc, under acetic acid peak), 1.81 (dd, J=12.4, 12.4 Hz, 1H, H-3(ax) NeuAc), 1.60 (bm, 2H, alkyl), 1.27 (bm, 10H, alkyl), 1.16 (bd, J=4.4 Hz, 3H, H-6 Fuc), 0.84 (bt, 3H, CH$_3$alkyl).

XXIV: Decyl (sodium (5-acetamido-3,5-dideoxy-α-D-glycero-D-galacto-2-nonulopyranosylonate)-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside.

$^1$H NMR (D$_2$O, 300 MHz) δ5.11 (bd, 1H, H-1 Fuc), 4.71 (bm, 2H, under water peak), 4.52 (d, J=7.7 Hz, 1H, H-1 Gal), 4.36 (d, J=7.9 Hz, 1H, H-1 Gal) 4.16 (bd, 1H, H-4 Gal), 4.11–3.49 (m, 29H), 2.75 (dd, J=12.4, 4.5 Hz, 1H, H-3(eq) (NeuAc), 2.02 (bs, 6H, NHAc), 1.78 (dd, J=12.4, 12.4 Hz, 1H, H-3(ax) NeuAc), 1.60 (bm, 14H, alkyl), 1.17 (bd, 3H, H-6 Fuc), 0.84 (bt, 3H, CH$_3$ alkyl).

The synthesis of compounds XXV and XXVI reacted alkyl 2,4-di-O-acetyl-β-D-galactopyranoside, where alkyl is either dodecyl or octadecyl, with 4-O-(2,3,4,6-tetra-O-acetyl-β-D-galactopyranosyl)-3,6-di-O-acetyl-2-deoxy-2-phthalimido-β-D-glucopyranosyl chloride to produce the trisaccharide using conditions similar to those used for compound VI. Enzymatic sialylation, as described for compound VII, and fucosidation then provided the pentasaccharides XXV and XXVI, respectively.

XXV: Dodecyl (sodium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3) )-O-(2-acetamido-2-deoxy-β-D-glucopyranosyl)-(1-3)-O-β-D-galactopyranoside.

$^1$H-NMR (300 MHz, δ in ppm relative to CD$_2$HOD) 5.02 (d, J=4 Hz, 1H), 4.65 (d, J=8 Hz, 1H), 4.50 (d, J=8 Hz, 1H), 4.20 (d, J=8 Hz, 1H), 4.05–3.30 (m), 2.85 (dd, J=4 Hz, J=12.4 Hz, 1H), 2.02 (s, 3H), 1.97 (s, 3H), 1.70 (dd, J=12.4 Hz, J=12.4 Hz, 1H), 1.60 (m, 2H), 1.35 (m, 20H), 1.20 (d, J=7 Hz, 3H), 0.92 (t, J=6 Hz, 3H).

XXVI: Octadecyl (sodium (5-acetamido-3,5-dideoxy-α-D-glycero-D-galacto-2-nonulopyranosylonate) )-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside.

$^1$H-NMR (300 MHz, δ in ppm relative to CD$_2$HOD) 5.02 (d, J=4 Hz, 1H), 4.65 (d, J=8 Hz, 1H), 4.50 (d, J=8 Hz, 1H), 4.20 (d, J=8 Hz, 1H), 4.05–3.30 (m), 2.85 (dd, J=4 Hz, J=12.4 Hz, 1H), 2.02 (s, 3H), 1.97 (s, 3H), 1.70 (dd, J=12.4 Hz, J=12.4 Hz, 1H), 1.60 (m, 2H), 1.35 (m, 36H), 1.20 (d, J=7 Hz, 3H), 0.92 (t, J=6 Hz, 3H).

EXAMPLE 2

This example illustrates the preparation of esterified forms of compound Z beginning with Ethyl (sodium (5-acetamido-3,5-dideoxy-α-D-glycero-D-galacto-nonulopyranosylonate))-(2-3)-O-(β-D-galactopyranosyl)-(1-4)-O-(2-allyloxycarbonylamino-2-deoxy-β-D-glucopyranosyl)-(1-3)-O-β-D-galactopyranoside (VII).

An aqueous solution (40 L) of ethyl (sodium (5-acetamido-3,5-dideoxy-α-D-glycero-D-galacto-nonulopyranosylonate))-(2-3)-O-(β-D-galactopyranosyl)-(1-4)-O-(2-allyloxycarbonylamino-2-deoxy-β-D-glucopyranosyl)-(1-3)-O-β-D-galactopyranoside (VII) produced from the sequential action of galactosyl and sialyl transferases in the presence of the appropriate cofactors on the disaccharide (V) (0.320 kg)

was filtered through paper. The filtrate was evaporated to a thick syrup in a 50 L rotavapor. The syrup was coevaporated twice with pyridine (2×2 L), then kept under vacuum for 20 hours. The evaporation flask was charged with a solution of N,N-dimethylaminopyridine (20 g) in pyridine (12 L). The rotavapor bath was charged with ice-water mixture, and rotation was continued while acetic anhydride (6 L) was added during a period of 1 hour. Two hours after complete addition more acetic anhydride (2 L) was added and the resulting mixture was left for 20 hours rotating slowly at room temperature. To ensure complete acetylation, more acetic anhydride (1 L) was added and the mixture was rotated for an additional 24 hours. The reaction was checked by TLC (ethyl acetate:hexane:ethanol, 10:10:3). Upon complete reaction vacuum was applied and 14 L of distillate collected.

To the resulting residue, an alcohol (15 L) is added over a period of 1 hour and the mixture is rotated at room temperature for 20 hours or until TLC on silica gel (ethyl acetate:hexane:ethanol, 10:10:3 and dichloromethane:acetone 3:2) shows complete conversion of the lactone to a slower-moving spot which is the ester mono hydroxy compound. The mixture is then concentrated (18 L evaporated) and cooled in ice water while acetic anhydride (3 L) is added over a period of 30 minutes. The mixture is left for 20 hours or until TLC on silica gel (dichloromethane:acetone 3:2) shows complete acylation. Alcohol (1 L) is added to destroy excess acetic anhydride during which a slight exotherm is typically noticed. After 1 hour, the mixture is concentrated to a syrup, and transferred to a 50 L extractor with the aid of ethyl acetate-water mixture (13/13 L). The mixture is agitated vigorously. After phase separation, the lower aqueous layer is drawn off, and the remaining organic layer is filtered through paper. The filtrate is washed with 5% aqueous hydrochloric acid (15 L, the aqueous layer should still be strongly acidic to pH-paper after washing), and aqueous 1M sodium bicarbonate (15 L, the aqueous layer should still be alkaline to pH paper after washing). The organic layer is then transferred to a 20 L container and dried over anhydrous sodium sulfate and filtered. The filtrate is concentrated to a semi-solid residue. This residue is dissolved in diehloromethane (3 L), and applied to a silica gel column (10 kg), packed in dichloromethane and eluted first with dichloromethane (25 L), then with 3:1 dichloromethane:acetone (25 L), and finally with 1:1 dichloromethane:acetone (50 L) to give fractions containing product. The fractions containing product are evaporated, and redissolved in dichloromethane (1.5 L). This solution is slowly added to a vigorously stirred mixture of ethyl ether (7.5 L) and hexane (10 L). The resulting precipitate is filtered and washed with 2:1 ether:hexane, air-dried overnight, then dried in high vacuum for 48 hours to provide a purified product of the ester-form of the blocked tetrasaccharide.

To a solution of blocked tetrasaccharide (0.37 mol) in dry tetrahydrofuran (8 L) is added polymethylhydrosiloxane (PMSH, 46 mL, 0.14 mol). Pd(PPH$_3$)$_4$ (14 g, 1.17 mmol) is then added and the mixture is degassed under vacuum. The resulting reaction mixture is then stirred at room temperature for 17 hours or until TLC (10:10:3, ethyl acetate:hexane:ethanol) shows completion of the reaction. To the reaction mixture is added acetic acid (36 mL, 0.55 mol) and piperidine (60 mL, 0.65 mol). The mixture is stirred at room temperature overnight or until TLC (95:5, dichloromethane:methanol) shows completion of the reaction. Evaporation of solvent in vacuo gives a residue which is dissolved in dichloromethane (4 L). This solution is washed successively with water (4 L), 2% aqueous hydrochloric acid (4 L), aqueous sodium hydrogen carbonate (4 L), and finally water (4 L). The organic layer is dried over anhydrous sodium sulfate, filtered and the filtrate is evaporated to give a syrup. This syrup is dissolved in methanol (2 L), activated charcoal (200 g) is added and the resulting mixture is heated with stirring to 55° C. for 2 hours. After cooling the mixture is filtered and the filtrate is concentrated to give a residue. This residue is dissolved in dichloromethane (1 L) and added dropwise to a mixture of hexane:ether (1:1, 12 L) to give Ethyl (alkyl (5-acetamido-3,5-dideoxy-4,7,8,9-tetra-O-acetyl-α-D-glycero-D-galacto-2-nonulopyanosylonate))-(2,3)-O-(3,4,6-tri-O-acetyl-β-D-galactopyranosyl)-(1,4)-O-(2-acetamido-2-deoxy-6-O-acetyl-β-D-glucopyranosyl)-(1,3)-O-(2,4,6-tri-O-acetyl-β-D-galactopyranoside) (referred to hereinafter as "alcohol IXa").

To a solution of the alcohol (IXa) (0.090 mol) in a mixture of dichloromethane (250 mL) and dimethylformamide (60 mL) is added tetraethylammonium bromide (18.8 g, 0.090 mol). The mixture is then stirred with molecular sieves (4A, 0,250 kg) under nitrogen at room temperature for 6 hours. To the above mixture is added freshly prepared tri-O-benzyl-α-L-fucopyranosyl bromide (0.180 kg, 0.360 mol) in dichloromethane (100 mL). The reaction mixture is then stirred under nitrogen at room temperature for 36 hours or until TLC (10:10:3, ethyl acetate:hexane:ethanol) shows completion of the reaction. The reaction mixture is treated with a mixture of methanol (30 mL) and diisopropylethylamine (30 mL) and is stirred at room temperature for 30 minutes. The mixture is diluted with 1 L of dichloromethane and filtered through a bed of celite. The filtrate is washed with aqueous saturated sodium bicarbonate (1.5 L) and water (2 L), and the organic layer is dried over magnesium sulfate, filtered, and concentrated to a syrup. This syrup is chromatographed on silica gel (3.5 kg silica gel, 230–400 mesh, ethyl acetate:hexane:ethanol, 5:5:1) to give Ethyl (alkyl (5-acetamido-3,5-dideoxy-4,7,8,9-tertra-O-acetyl-α-D-glycero-D-galacto-2-nonulopyanosylonate))-(2-3)-O-(2,4,6-tri-O-acetyl-β-D-galactopyranosyl)-(1-4)-O-((2,3,4-tri-O-benzyl-α-L-fucopyranosyl)-(1-3)-O-(2-acetamindo-6-O-acetyl-2-deoxy-β-D-glucopyranosyl)-(1-3)-O-2,4,6-tri-O-acetyl-β-D-galactopyranoside (referred to hereinafter as esterpentasaccharides, "Xa").

To a solution of an ester-pentasaccharide, Xa (61 mmol) in acetic acid (900 mL) is added palladium hydroxide on charcoal (20 g, 20% dl). The reaction mixture is purged two times with hydrogen and then stirred under a hydrogen atmosphere for 8 hours or until TLC (90:10, dichloromethane:methanol) shows completion of the reaction. The reaction vessel is purged several times with nitrogen and the reaction mixture is filtered through a bed of celite to remove the catalyst. The celite pad is washed with ethyl acetate several times. Concentration of the filtrate gives the debenzylated product. The product is dried over high vacuum overnight and is dissolved in ethyl acetate (500 mL). The product triol is then precipitated out with addition of 1 L of a mixture of ether and hexane (8:2).

To a solution of the triol (50 mmol) in alcohol (1 L) is added a solution of an alkoxide (70 mL, about 25% w/v). The reaction mixture is stirred at room temperature for 17 hours. To the reaction mixture is added 150 mL of AG-50 H+ ion-exchange resin, which has been thoroughly washed with the alcohol, and the resulting mixture is stirred at room temperature for 30 minutes. The ion-exchange resin is removed by filtration and filtrate is concentrated to dryness. The material is dissolved in the alcohol (300 mL), or a mixture of an alcohol in acetonitrile or THF, and filtered through a 0.22 μ nylon membrane. The filtrate is diluted with ethyl ether (300 mL) to give the prodrug pentasaccharide esters having the formula:

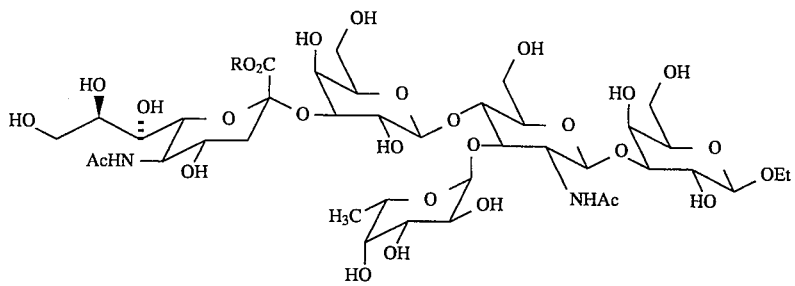

in which R is the alkyl group derived from the alcohol and alkoxide used in preparation.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A pharmaceutical composition comprising a pharmaceutically acceptable carrier and a compound having the formula:

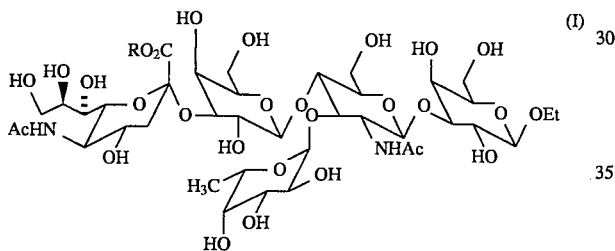

in which R is an alkyl group.

2. A composition in accordance with claim 1, wherein R is a member selected from the group consisting of methyl, ethyl, propyl, isopropyl, butyl, isobutyl, tert-butyl, benzyl, pentyl and hexyl.

3. A compound having the formula:

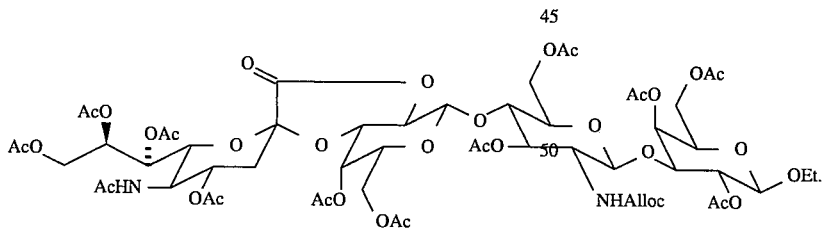

4. A compound having the formula:

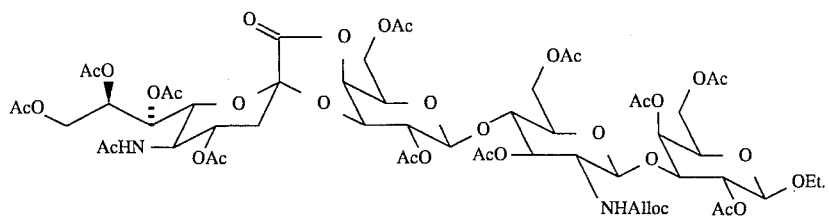

5. A compound having the formula:

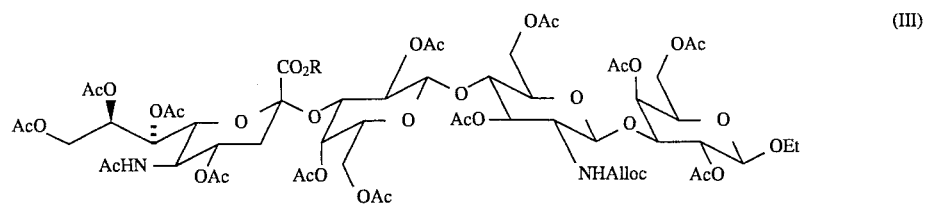
(III)

in which R is alkyl.

6. A compound in accordance with claim 5, wherein R is selected from the group consisting of methyl, ethyl, propyl, butyl and pentyl.

7. A method of preparing pharmaceutical agents, said pharmaceutical agents having the formula:

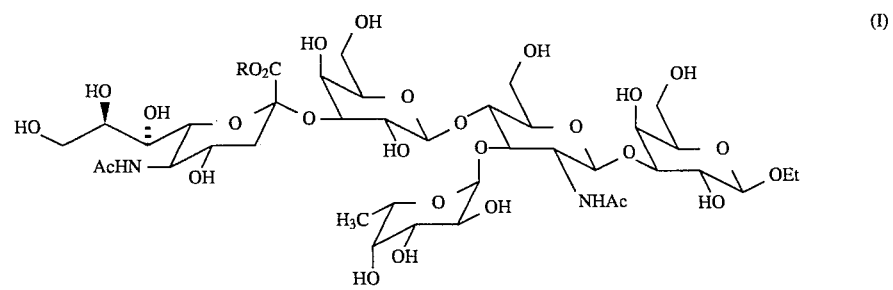
(I)

in which R is alkyl, said method comprising:
  (a) treating a lactone intermediate selected from the group consisting of lactones of formula

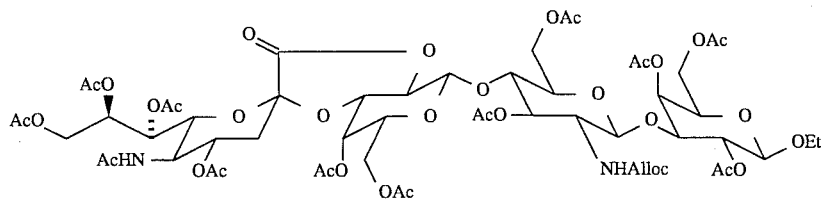

and

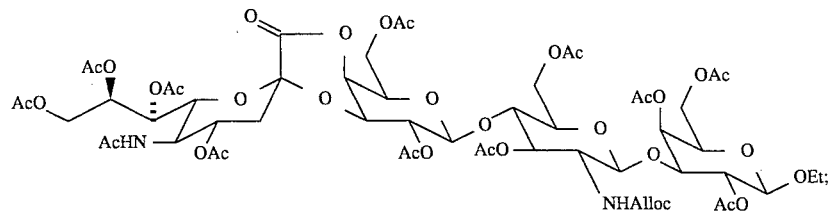

with an alkoxide to form an ester intermediate having the formula:

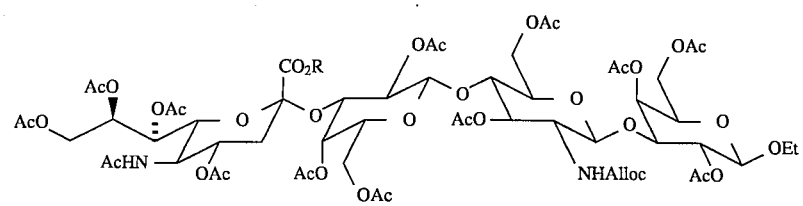

wherein R is an alkyl group derived from said alkoxide; and (b) deprotecting and fucosylating the ester intermediate produced in step (a) to provide said pharmaceutical agents.

8. A method for the one-pot conversion of Ethyl (methyl (5-acetamido-3,5-dideoxy-4,7,8,9-tetra-O-acetyl-α-D-glycero-D-galacto-nonulopyranosylonate) )-(2-3)-O-(2,4,6-tri-O-acetyl-β-D-galactopyranosyl)-(1-4)-O-(3,6-di-O-acetyl-2-allyloxycarbonylamino-2-deoxy-β-D-glucopyranosyl)-(1-3)-O-2,4,6-tri-O-acetyl-β-D-galactopyranoside to Ethyl (methyl (5-acetamido-3,5-dideoxy-4,7,8,9-tetra-0-acetyl-α-D-glycero-D-galacto-2-nonulopyanosylonate))-(2,3)-0-(3,4,6-tri-0-acetyl-β-D-galactopyranosyl)-(1,4)-0-(2-acetamido-2-deoxy-6-0-acetyl-β-D-glucopyranosyl)-(1,3)-0-2,4,6-tri-0-acetyl-β-D-galactopyranoside, comprising:

contacting said Ethyl (methyl (5-acetamido-3,5-dideoxy-4,7,8,9-tetra-O-acetyl-α-D-glycero-D-galacto-nonulopyranosylonate))-(2-3)-O-(2,4,6-tri-O-acetyl-β-D-galactopyranosyl)-(1-4)-O-(3,6-di-O-acetyl-2-allyloxycarbonylamino-2-deoxy-β-D-glucopyranosyl)-(1-3)-O-2,4,6-tri-O-acetyl-β-D-galactopyranoside sequentially with polymethylhydrosiloxane and tetrakis triphenylphosphine palladium (0) followed by acetic acid and pyridine, under conditions sufficient to produce said Ethyl (methyl (5-acetamido(3,5-dideoxy-4,7,8,9-tetra-0-acetyl-α-D-glycero-D-galacto-2-nonulopyanosylonate))-(2,3)-O-(3,4,6-tri-0-acetyl-β-D-galactopyranosyl)-(1,4)-0-(2-acetamido-2-deoxy-6-0-acetyl-β-D-glucopyranosyl)-(1,3)-0-2,4,6-tri-O-acetyl-β-D-galactopyranoside.

* * * * *